United States Patent

Broughton et al.

[11] Patent Number: 6,143,773
[45] Date of Patent: *Nov. 7, 2000

[54] SUBSTITUTED THIENOBENZISOXAZOLE DERIVATIVES FOR ENHANCING COGNITION

[75] Inventors: Howard Barff Broughton, Harlow; Mark Stuart Chambers, Puckeridge, both of United Kingdom

[73] Assignee: Merck Sharp & Dohme Limited, Hertfordshire, United Kingdom

[*] Notice: This patent issued on a continued prosecution application filed under 37 CFR 1.53(d), and is subject to the twenty year patent term provisions of 35 U.S.C. 154(a)(2).

[21] Appl. No.: 09/296,848

[22] Filed: Apr. 22, 1999

[30] Foreign Application Priority Data

Apr. 23, 1998 [GB] United Kingdom .................. 9808663

[51] Int. Cl.[7] .......................... C07D 495/04; A61K 31/42
[52] U.S. Cl. .......................... 514/379; 548/242; 546/270; 544/140; 544/368
[58] Field of Search ............. 548/242; 514/379; 546/270; 544/140, 368

[56] References Cited

U.S. PATENT DOCUMENTS 5,587,486  12/1996  Mills, et al. .

FOREIGN PATENT DOCUMENTS 221414     5/1987  European Pat. Off. ............... 548/242
WO 96/16954  6/1996  WIPO .
WO 98/18792  5/1998  WIPO .

OTHER PUBLICATIONS

Van Rhee, et al., J. Med. Chem., vol., 39, pp. 398–406, 1996.

Primary Examiner—Robert Gerstl
Attorney, Agent, or Firm—Shu M. Lee; Philippe L. Durette; Melvin Winokur

[57] ABSTRACT

The present invention provides compounds of formula (I) and pharmaceutically acceptable salts thereof:

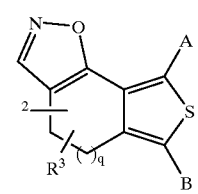

(I)

wherein A is $C_{1-6}$alkyl, $C_{2-6}$alkenyl, $C_{2-6}$alkynyl, $C_{3-6}$cycloalkyl, aryl$C_{1-6}$alkyl, aryl, $S(O)_pR^1$, $OR^1$ or $NR^1R^{12}$;

B is optionally substituted 5- or 6-membered heteroaromatic ring or $C(O)NR^{10}R^{11}$;

$R^1$ is hydrogen, optionally substituted $C_{1-6}$alkyl, $C_{2-6}$alkenyl, $C_{2-6}$alkynyl, $C_{3-6}$cycloalkyl or $C_{3-6}$cycloalkenyl, optionally substituted aryl, aryl$C_{1-6}$alkyl, aryl$C_{2-6}$alkenyl or aryl$C_{2-6}$alkynyl or an optionally substituted 5- or 6-membered heteroaromatic ring;

$R^2$ and $R^3$ are hydrogen or $C_{1-6}$alkyl;

$R^4$ is hydrogen, $C_{1-8}$alkyl, $C_{2-8}$alkenyl, $C_{2-8}$alkynyl, aryl or $CH_2(CO)_mNR^8R^9$;

$R^5$ is $NR^6R^7$, $C_{1-6}$alkyl or $C_{1-6}$alkoxy;

$R^6$ is independently as defined for $R^4$;

$R^7$ is aryl optionally substituted by halogen, nitro or cyano;

$R^8$ is hydrogen, $C_{1-6}$alkyl, $C_{3-6}$cycloalkyl, $C_{3-6}$cycloalkenyl, $C_{2-6}$alkenyl, $C_{2-6}$alkynyl; aryl$C_{1-6}$alkyl, aryl$C_{2-6}$alkenyl or aryl$C_{2-6}$alkynyl optionally substituted on the aryl ring by halogen, nitro or cyano; thiophene or pyridine;

$R^9$ is $C_{1-6}$alkyl; $C_2$.alkenyl; $C_{2-6}$alkynyl; or phenyl optionally substituted by one, two or three substituents independently chosen from halogen, $CF_3$, $OCH_3$, nitro and cyano;

$R^{10}$ and $R^{11}$ are individually hydrogen, $C_{1-6}$alkyl, $C_{2-6}$alkenyl, $C_{2-6}$alkynyl or $C_{3-8}$cycloalkyl or $R^{10}$ and $R^{11}$, together with the nitrogen atom to which they are attached, form a saturated 4 to 8 membered ring optionally containing an oxygen atom or a further nitrogen atom as a ring member, the further nitrogen atom being unsubstituted or substituted by $C_{1-4}$alkyl, $C_{2-4}$alkenyl or $C_{2-4}$alkynyl;

$R^{12}$ is hydrogen or $C_{1-6}$alkyl;

m is zero or 1;
p is zero, 1 or 2;
q is 0, 1 or 2; and
r is 0, 1 or 2;

the preparation of these compounds, their use in enhancing cognition in disease states, particularly Alzheimer's disease, and methods of treatment using them.

6 Claims, No Drawings

SUBSTITUTED THIENOBENZISOXAZOLE DERIVATIVES FOR ENHANCING COGNITION

The present invention relates to pharmaceutical compounds which are generally substituted thienobenzoisoxazole derivatives and to their use in therapy. More particularly, this invention is concerned with substituted derivatives which are ligands for $GABA_A$ receptors, in particular for $GABA_A$ $\alpha 5$ receptors and are therefore useful in therapy particularly where cognition enhancement is required.

Receptors for the major inhibitory neurotransmitter, gamma-aminobutyric acid (GABA), are divided into two main classes: (1) $GABA_A$ receptors, which are members of the ligand-gated ion channel superfamily; and (2) $GABA_B$ receptors, which may be members of the G-protein linked receptor superfamily. Since the first cDNAs encoding individual $GABA_A$ receptor subunits were cloned the number of known members of the mammalian family has grown to thirteen (six $\alpha$ subunits, three $\beta$ subunits, three $\gamma$ subunits and one $\delta$ subunit). It may be that further subunits remain to be discovered; however, none has been reported since 1993.

Although knowledge of the diversity of the $GABA_A$ receptor gene family represents a huge step forward in our understanding of this ligand-gated ion channel, insight into the extent of subtype diversity is still at an early stage. It has been indicated that an $\alpha$ subunit, a $\beta$ subunit and a $\gamma$ subunit constitute the minimum requirement for forming a fully functional $GABA_A$ receptor expressed by transiently transfecting cDNAs into cells. As indicated above, a $\delta$ subunit also exists, but is apparently uncommon in the native receptor.

Studies of receptor size and visualisation by electron microscopy conclude that, like other members of the ligand-gated ion channel family, the native $GABA_A$ receptor exists in pentameric form. The selection of at least one $\alpha$, one $\beta$ and one $\gamma$ subunit from a repertoire of thirteen allows for the possible existence of more than 10,000 pentameric subunit combinations. Moreover, this calculation overlooks the additional permutations that would be possible if the arrangement of subunits around the ion channel had no constraints (i.e. there could be 120 possible variants for a receptor composed of five different subunits).

Receptor subtype assemblies which do exist include $\alpha 1\beta 2\gamma 2$, $\alpha 2\beta 2/3\gamma 2$, $\alpha 3\beta\gamma 2/3$, $\alpha 2\beta\gamma 1$, $\alpha 5\beta 3\gamma 2/3$, $\alpha 6\beta\gamma 2$, $\alpha 6\beta\delta$ and $\alpha 4\beta\delta$. Subtype assemblies containing an $\alpha 1$ subunit are present in most areas of the brain and account for over 40% of $GABA_A$ receptors in the rat. Subtype assemblies containing $\alpha 2$ and $\alpha 3$ subunits respectively account for about 25% and 17% of $GABA_A$ receptors in the rat. Subtype assemblies containing an $\alpha 5$ subunit are primarily hippocampal and represent about 4% of receptors in the rat.

A characteristic property of some $GABA_A$ receptors is the presence of a number of modulatory sites, of which the most explored is the benzodiazepine (BZ) binding site through which anxiolytic drugs such as diazepam and temazepam exert their effect. Before the cloning of the $GABA_A$ receptor gene family, the benzodiazepine binding site was historically subdivided into two subtypes, BZ1 and BZ2, on the basis of radioligand binding studies. The BZ1 subtype has been shown to be pharmacologically equivalent to a $GABA_A$ receptor comprising the $\alpha 1$ subunit in combination with $\beta 2$ and $\gamma 2$. This is the most abundant $GABA_A$ receptor subtype, representing almost half of all $GABA_A$ receptors in the brain.

Two other major populations are the $\alpha 2\beta\gamma 2$ and $\alpha 3\beta\gamma 2/3$ subtypes. Together these constitute approximately a further 35% of the total $GABA_A$ receptor repertoire. Pharmacologically this combination appears to be equivalent to the BZ2 subtype as defined previously by radioligand binding, although the BZ2 subtype may also include certain $\alpha 5$-containing subtype assemblies. The physiological role of these subtypes has hitherto been unclear because no sufficiently selective agonists or antagonists were known.

It is now believed that agents acting as BZ agonists at $\alpha 1\beta\gamma 2$, $\alpha 2\beta\gamma 2$ or $\alpha 3\beta\gamma 2$ subunits will possess desirable anxiolytic properties. The $\alpha 1$-selective $GABA_A$ receptor agonists alpidem and zolpidem are clinically prescribed as hypnotic agents, suggesting that at least some of the sedation associated with known anxiolytic drugs which act at the BZ1 binding site is mediated through $GABA_A$ receptors containing the $\alpha 1$ subunit. Accordingly, it is considered that $GABA_A$ receptor agonists which bind more effectively to the $\alpha 2$ and/or $\alpha 3$ subunit than to $\alpha 1$ will be effective in the treatment of anxiety with a reduced propensity to cause sedation. Also, agents which are antagonists or inverse agonists at $\alpha 1$ might be employed to reverse sedation or hypnosis caused by $\alpha 1$ agonists.

A number of dementing illnesses such as Alzheimer's disease are characterised by a progressive deterioration in cognition in the sufferer. It would clearly be desirable to enhance cognition in subjects desirous of such treatment, for example for subjects suffering from a dementing illness. It is believed this can be done utilising compounds which are ligands for the $GABA_A$ $\alpha 5$ receptor subtype.

WO-A-9616954 mentions three thienylcyclohexanone derivatives substituted by substituted arylaminocarbonyl on the thiophene ring as fungicides.

Van Rhee et al, *J. Med. Chem.*, 1996, 39, 398–406 discloses related compounds as adenosine receptor antagonists which differ in having an ester group on the thiophene ring.

The present invention provides compound of formula (I) or a pharmaceutically acceptable salt thereof:

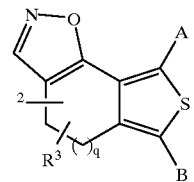

where A is $C_{1-6}$alkyl, $C_{2-6}$alkenyl, $C_{2-6}$alkynyl, $C_{3-6}$cycloalkyl, aryl$C_{1-6}$alkyl, aryl, $S(O)_pR^1$, $OR^1$ or $NR^1R^{12}$;

B is a 5-membered ring having one or two unsaturations containing 1, 2, 3 or 4 heteroatoms chosen from O, N and S provided that not more than one heteroatom is other than N, or a 6-membered aromatic ring containing 1 or 2 nitrogen atoms, which ring is optionally substituted by one or more substituents independently chosen from: $C_{1-6}$alkyl; $C_{1-6}$haloalkyl; halogen; $S(O)_pR^4$; $COR^5$; and aryl or aryl $C_{1-6}$alkyl wherein the aryl ring is optionally substituted by one, two or three substituents independently chosen from halogen, $CF_3$, $OCH_3$, nitro and cyano; or B is a group $C(O)NR^{10}R^{11}$;

$R^1$ is hydrogen; $C_{1-6}$alkyl, $C_{2-6}$alkenyl, $C_{2-6}$alkynyl, $C_{3-6}$cycloalkyl or $C_{3-6}$cycloalkenyl each of which is optionally substituted by amino, $C_{1-6}$alkylamino, di($C_{1-6}$alkyl)amino, $C_{1-6}$alkoxy, $C_{1-6}$-alkylaminocarbonyl, one, two or three hydroxy groups, one, two or three halogen atoms or a four, five or six-membered saturated heterocyclic ring containing a nitrogen atom and optionally either an oxygen atom or a further nitrogen atom which ring is optionally substituted by $C_{1-4}$alkyl on the further nitrogen atom; aryl, aryl$C_{1-6}$alkyl, aryl$C_{2-6}$alkenyl or aryl$C_{2-6}$alkynyl optionally substituted on the aryl ring by halogen, nitro, cyano, $C_{1-6}$alkylcarbonylamino, hydroxy or $C_{1-6}$alkoxy; or a five-membered aromatic ring containing 1, 2, 3 or 4 heteroatoms chosen from O, N and S provided that not more than one heteroatom is other than N, or a six-membered aromatic ring containing 1, 2, 3 or 4 nitrogen atoms, either of which rings is optionally substituted by halogen, $C_{1-6}$alkoxy, $C_{1-6}$alkylthio, aryl, $C_{1-6}$alkyl, $C_{2-6}$alkenyl or $C_{2-6}$alkynyl;

$R^2$ and $R^3$ are independently hydrogen or $C_{1-6}$alkyl or together with the carbon atom to which they are attached form a $C_{3-8}$cycloalkyl group;

$R^4$ is hydrogen, $C_{1-8}$alkyl, $C_{2-8}$alkenyl, $C_{2-8}$alkynyl, aryl or $CH_2(CO)_m NR^8R^9$;

$R^5$ is $NR^6R^7$, $C_{1-6}$alkyl or $C_{1-6}$alkoxy;

$R^6$ is independently as defined for $R^4$;

$R^7$ is aryl optionally substituted by halogen, nitro or cyano;

$R^8$ is hydrogen, $C_{1-6}$alkyl, $C_{3-6}$cycloalkyl, $C_{3-6}$cycloalkenyl, $C_{2-6}$alkenyl, $C_{2-6}$alkynyl; aryl$C_{1-6}$alkyl, aryl$C_{2-6}$alkenyl or aryl$C_{2-6}$alkynyl optionally substituted on the aryl ring by halogen, nitro or cyano; thiophene or pyridine;

$R^9$ is $C_{1-6}$alkyl; $C_{2-6}$alkenyl; $C_{2-6}$alkynyl; or phenyl optionally substituted by one, two or three substituents independently chosen from halogen, $CF_3$, $OCH_3$, nitro and cyano;

$R^{10}$ and $R^{11}$ are individually hydrogen, $C_{1-6}$alkyl, $C_{2-6}$alkenyl, $C_{2-6}$alkynyl or $C_{3-8}$cycloalkyl or $R^{10}$ and $R^{11}$, together with the nitrogen atom to which they are attached, form a saturated 4 to 8 membered ring optionally containing an oxygen atom or a further nitrogen atom as a ring member, the further nitrogen atom being unsubstituted or substituted by $C_{1-4}$alkyl, $C_{2-4}$alkenyl or $C_{2-4}$alkynyl;

$R^{12}$ is hydrogen or $C_{1-6}$alkyl;

m is zero or 1;

p is zero, 1 or 2;

q is 0, 1 or 2; and r is 0, 1 or 2.

B is preferably a 5- or 6-membered optionally substituted aromatic ring.

Thus when B is an aromatic ring it may be a thiazole, pyrazole, pyrimidine, tetrazole, triazole, oxadiazole, oxazole, pyridine, imidazole or pyrazine which is unsubstituted or substituted by $C_{1-6}$alkyl, halogen, $SR^4$, $COR^5$ or benzyl optionally substituted by halogen. When B is a 5- or 6-membered ring having one unsaturation it is preferably oxazolidinyl or imidazolinyl optionally substituted by halogen or $C_{1-4}$alkyl.

Particular embodiments of B are (1-phenylsulphonyl) pyrazol-3-yl, 1-acetylpyrazol-3-yl, (3-ethoxycarbonyl) isoxazol-5-yl, (3-isopropyl)-1,2,4-oxadiazol-5-yl, imidazolin-2-yl, pyrazol-4-yl, 2-methyl-1,3,4-oxadiazol-5-yl, oxazolidin-2-yl, 2-methyltetrazol-5-yl, pyrazol-3-yl, 2-propyltetrazol-5-yl, thiazol-2-yl, 4-methyl-1,2,4-triazol-3-yl, (4-ethoxycarbonyl)thiazol-2-yl, (4-trifluoromethyl) thiazol-2-yl, (4-acetyl)thiazol-2-yl, (4-methyl)thiazol-2-yl, pyrrol-2-yl, pyrid-2-yl, 3-methyl-1,2,4-oxadiazol-5-yl, 4-benzyl-1,2,4-triazol-3-yl, 1-methyl-1,2,4-triazol-3-yl, oxazol-2-yl, pyrazin-2-yl, pyrimidin-5-yl, 3-(N-methylaminocarbonyl)thiazol-2-yl, thiazol-5-yl, isoxazol-5-yl, pyrid-3-yl, pyrid-4-yl, 1,3,4-oxadiazol-5-yl and 1-methylsulphonylpyrazol-3-yl.

Favoured embodiments of B are pyrrolidinylcarboxyl, morpholinylcarboxyl, N,N-dimethylaminocarbonyl, N-methylpiperazinylcarbonyl, hexamethyleneiminocarbonyl, aminocarbonyl, pyridin-2-yl, 1-methyl-1,2,4-triazol-3-yl, pyridin-3-yl, 1-methylpyrazol-3-yl and thiazol-2-yl.

$R^1$ is preferably $C_{1-6}$alkyl, $C_{2-6}$alkenyl or $C_{3-6}$cycloalkyl each of which is optionally substituted by amino, di($C_{1-6}$alkyl)amino, hydroxy, $C_{1-6}$alkoxy, $C_{1-6}$alkylaminocarbonyl or one, two or three halogen atoms; aryl or aryl$C_{1-6}$alkyl optionally substituted on the aryl ring by halogen, $C_{1-6}$alkylcarbonylamino or $C_{1-6}$alkoxy; or a five-membered aromatic ring containing 1, 2 or 3 heteroatoms chosen from O, N and S provided that not more than one heteroatom is other than N, or a six-membered aromatic ring containing 1 or 2 nitrogen atoms, either of which rings is optionally substituted by halogen, $C_{1-6}$alkoxy, $C_{1-6}$alkylthio, aryl or $C_{1-6}$alkyl.

More preferably $R^1$ is $C_{1-6}$alkyl, $C_{1-4}$alkenyl, or $C_{3-6}$cycloalkyl each of which is optionally substituted by di($C_{1-4}$alkyl)amino, $C_{1-4}$alkoxy, $C_{1-4}$alkylaminocarbonyl, one or two hydroxy groups or three fluorine atoms; phenyl or phenyl$C_{1-4}$alkyl optionally substituted on the phenyl ring by chlorine, fluorine, $C_{1-4}$alkoxy or $C_{1-4}$alkylcarbonylamino; or a pyridine, thiophene, furan, pyrimidine, thiazole, imidazole, triazole or thiadiazole, each of which is unsubstituted or substituted by $C_{1-4}$alkyl, phenyl, fluorine or $C_{1-4}$alkylthio. Most preferably $R^1$ is $C_{1-6}$alkyl or phenyl.

A may be $S(O)_p R^1$, or $OR^1$ particularly $S(O)_p R^1$.

When A is not $S(O)_p R^1$, $OR^1$ or $NR^1R^{14}$ it is preferably $C_{1-6}$alkyl, $C_{2-6}$alkenyl or $C_{3-6}$cycloalkyl.

When A is $OR^1$, $R^1$ is generally $C_{1-6}$alkyl optionally substituted by $C_{1-4}$alkoxy, $C_{3-6}$cycloalkyl or aryl, particularly $C_{1-6}$alkyl.

Particular embodiments of A are phenyl, cyclohexyl, 2-methylprop-1-enyl, methylthio, ethyl, isopropyl, propyl, cyclobutyl, but-3-enyl, cyclopropyl, methanesulphonyl, methyl, benzyl, methanesulphonyl, (1,1-dimethylethyl)thio, pentylthio, (4-methyl-1,2,4-triazol-3-yl)thio, hexylthio, benzylamino, (3-imidazol-1-ylpropyl)amino, (pyrid-2-yl) amino, 2-methylprop-1-yl, [3-(4-methylpiperazin-1-yl) propyl]amino, methylamino, (2-hydroxyethyl)amino, azetidin-1-yl, tert-butylamino, isopropylthio, (2-hydroxyethyl)thio, methoxy, dimethylamino, cyclobutoxy, phenoxy, butylthio, (3-chloropropyl)thio, (2-phenylethyl)thio, propylthio, (2-methylbutyl)thio, (2,2,2-trifluoroethyl)thio, (1-methylpropyl)thio, (4-chlorophenyl) thio, (3-fluorophenyl)thio, (4-acetylaminophenyl)thio, (4-methoxyphenyl)thio, (1-methylimidazol-2-yl)thio, (thiophen-2-yl)thio, (imidazol-2-yl)thio, (4-phenylthiazol-2-yl)thio, (1,2,4-triazol-3-yl)thio, (5-methyl-1,3,4-thiadiazol-2-yl)thio, (5-methylthio-1,3,4-thiadiazol-2-yl)thio, benzylthio, cyclopentylthio, (2-methylpropyl)thio, (furan-2-ylmethyl)thio, (2-hydroxy-1-methylpropyl)thio, (2,3-dihydroxypropyl)thio, (2-hydroxypropyl)thio, ((N-methylaminocarbonyl)methyl)thio, (pyrid-4-yl)thio, (pyrimidin-2-yl)thio, (thiazol-2-yl)thio, prop-2-enylthio, (pyrid-2-yl)thio, ethylthio, phenylthio, (N,N-dimethyl-2-aminoethyl)thio, (2-methoxyethyl)thio, (furan-2-ylmethyl) amino, (2-methylpropyl)amino, propylamino, (2-methoxyethyl)amino, cyclopropylamino, isopropylamino, ethylamino, cyclobutylamino and isopropoxy.

Preferred embodiments of A are methylthio, phenylthio, propylthio, ethylthio, isopropylthio and ethoxy.

$R^2$ and $R^3$ are preferably independently chosen from hydrogen and methyl or are attached to the same carbon atom and together with that atom form a $C_{3-6}$cycloalkyl group, and are most preferably both methyl. Preferably $R^2$ and $R^3$ are geminal to each other, preferably at the 6-position, i.e. beta to the oxygen bearing carbon of the benzene residue in formula I.

$R^4$ may by hydrogen, $C_{1-4}$alkyl, $C_{2-4}$alkenyl, $C_{2-4}$alkynyl, aryl or $CH_2(CO)_m NR^8R^9$. $R^4$ is preferably hydrogen, $C_{1-4}$alkyl or $CH_2(CO)_m NR^8R^9$, more preferably hydrogen, methyl or $CH_2CONR^8R^9$ and most preferably methyl or $CH_2CONR^8R^9$.

$R^5$ is preferably methyl, methoxy, ethoxy or $NR^6R^7$ and most preferably methyl, ethoxy or $NR^6R^7$.

$R^6$ may be hydrogen, $C_{1-4}$alkyl, $C_{2-4}$alkenyl, $C_{2-4}$alkynyl, aryl or $CH_2(CO)_m NR^8R^9$. $R^6$ is preferably hydrogen or $C_{1-4}$alkyl and most preferably hydrogen.

$R^7$ is preferably phenyl unsubstituted or substituted by halogen, nitro or cyano, more preferably optionally substituted by halogen, such as chlorine.

$R^8$ is preferably hydrogen or $C_{1-6}$alkyl and most preferably hydrogen.

$R^9$ is preferably $C_{1-6}$alkyl or phenyl unsubstituted or substituted by one, two or three substituents independently chosen from halogen, nitro and cyano, more preferably $C_{1-6}$alkyl or phenyl optionally substituted by one or two substituents independently chosen from halogen and nitro and most preferably tert-butyl or phenyl optionally substituted with one or two substituents chosen from chlorine and nitro, such as 4-chlorophenyl.

$R^{10}$ and $R^{11}$ are preferably independently hydrogen, $C_{1-4}$alkyl or $C_{3-6}$cycloalkyl or $R^{10}$ and $R^{11}$, together with the nitrogen atom to which they are attached, form a saturated 5 to 7-membered ring optionally containing an oxygen atom or a further nitrogen atom at the 4-position, the further nitrogen atom being unsubstituted or substituted with $C_{1-4}$alkyl. More particularly $R^{10}$ and $R^{11}$ are independently hydrogen, methyl or cyclohexyl or $R^{10}$ and $R^{11}$ together with the nitrogen atom to which they are attached form a piperidine, hexamethyleneimine, piperazine or morpholine ring, the further nitrogen atom in the piperazine ring being optionally substituted by methyl.

Particular values of $NR^{10}R^{11}$ are pyrrolidine, morpholine, N,N-dimethylamine, N-methylpiperazine, hexamethyleneimine, N-methyl-N-cyclohexylamine and amine.

$R^{12}$ is generally hydrogen or $C_{1-4}$alkyl and most preferably hydrogen.

m is preferably 1.

p is preferably zero or two, most preferably zero.

q is preferably 1.

r is preferably 1.

The present invention also provides a subclass of compounds of formula I and the pharmaceutically acceptable salts thereof in which:

A is $S(O)_p R^1$ or $OR^1$;

B is a thiazole, pyrazole, pyrimidine, tetrazole, triazole, oxadiazole, oxazole, pyridine, imidazole or pyrazine which is unsubstituted or substituted by $C_{1-6}$alkyl or halogen, or B is $C(O)NR^{10}R^{11}$;

$R^1$ is $C_{1-6}$alkyl or phenyl;

$R^2$ and $R^3$ are independently hydrogen or methyl;

$R^{10}$ and $R^{11}$ are independently hydrogen, $C_{1-4}$alkyl or $C_{1-6}$cycloalkyl or $R^{10}$ and $R^{11}$, together with the nitrogen atom to which they are attached, form a saturated 5- to 7-membered ring optionally containing an oxygen atom or a further nitrogen atom at the 4-position, the further nitrogen atom being unsubstituted or substituted with $C_{1-4}$alkyl;

p is zero or 2; and q is one.

The preferred definitions of each substituent apply to this subclass mutatis mutandis.

The invention further provides a compound which is:
(4,4-dimethyl-8-methylthio-4,5-dihydrothieno[3,4-g]-1,2-benzisoxazol-6-yl)(pyrrolidin-1-yl)methanone;
(dimethylamino)(4,4-dimethyl-8-methylthio-4,5-dihydrothieno[3,4-g]-1,2-benzisoxazol-6-yl)methanone;
(4,4-dimethyl-8-methylthio-4,5-dihydrothieno[3,4-g]-1,2-benzisoxazol-6-yl)([N-methyl]cyclohexylamino) methanone;
(4,4-dimethyl-8-ethoxy-4,5-dihydrothieno[3,4-g]-1,2-benzisoxazol-6-yl) (pyrrolidin-1-yl) methanone;
4,4-dimethyl-8-methylthio-4,5-dihydrothieno[3,4-g]-1,2-benzisoxazol-6-yl)(homopiperidin-1-yl)methanone;
(4,4-dimethyl-8-isopropylthio-4,5-dihydrothieno[3,4-g]-1,2-benzisoxazol-6-yl)(pyrrolidin-1-yl)methanone;
(4,4-dimethyl-8-methylthio-4,5-dihydrothieno[3,4-g]-1,2-benzisoxazol-6-yl)(morpholin-4-yl)methanone;
(4,4-dimethyl-8-methylthio-4,5-dihydro-thieno[3,4-g]-1,2-benzisoxazol-6-yl)(4-methylpiperazin-1-yl)methanone;
8-methylthio-6-(thiazol-2-yl)-4,5-dihydrothieno[3,4-g]-1,2-benzisoxazole;
(4,4-dimethyl-8-phenylthio-4,5-dihydrothieno[3,4-g]-1,2-benzisoxazol-6-yl)(pyrrolidin-1-yl)methanone;
(4,4-dimethyl-8-ethylthio-4,5-dihydrothieno[3,4-g]-1,2-benzisoxazol-6-yl)(pyrrolidin-1-yl)methanone;
(4,4-dimethyl-8-propylthio-4,5-dihydrothieno[3,4-g]-1,2-benzisoxazol-6-yl)(pyrrolidin-1-yl)methanone;
4,4-dimethyl-8-methylthio-6-(pyrid-2-yl)-4,5-dihydrothieno[3,4-g]-1,2-benzisoxazole;
4,4-dimethyl-8-methylthio-6-(pyrid-3-yl)-4,5-dihydrothieno[3,4-g]-1,2-benzisoxazole;
4,4-di methyl-6-(1-methylpyrazol-3-yl)-8-methylthio-4,5-dihydrothieno[3,4-g]-1,2-benzisoxazole; or
4,4-dimethyl-8-methylthio-6-(1-methyl-1,2,4-triazol-3-yl)-4,5-dihydrothieno[3,4-g]-1,2-benzisoxazole;
or a pharmaceutically acceptable salt thereof.

Preferably the compositions according to the present invention are in unit dosage forms such as tablets, pills, capsules, powders, granules, solutions or suspensions, or suppositories, for oral, parenteral or rectal administration, by inhalation or insufflation or administration by transdermal patches or by buccal cavity absorption wafers.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil, peanut oil or soybean oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatin.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are administered by the oral or nasal respiratory route for local or systemic effect. Compositions in preferably sterile pharmaceutically acceptable solvents may be nebulised by use of inert gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

Compositions of the present invention may also be presented for administration in the form of trans-dermal patches using conventional technology. The compositions may also be administered via the buccal cavity using, for example, absorption wafers.

In disorders associated with $GABA_A$ $\alpha$ receptors, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The present invention also provides a process for the preparation of a pharmaceutical composition which comprises adding a compound of formula (I) or a pharmaceutically acceptable salt thereof to a pharmaceutically acceptable excipient.

The present invention also provides a compound of formula (I) or a pharmaceutically acceptable salt thereof for use in a method of treatment of the human or animal body, in particular for the treatment or prevention of conditions for which the administration of a cognition enhancing agent is desirable, such as Alzheimer's disease.

The compounds of formula (I) are of potential value in the treatment or prevention of a wide variety of clinical conditions which can be alleviated by a ligand selective for $GABA_A$ receptors containing the ($\alpha$5 subunit. In particular, they are desirably inverse agonists of the $\alpha$5 subunit.

Thus, for example, such a ligand can be used in a variety of disorders of the central nervous system. Such disorders include delirium, dementia and amnestic and other cognitive disorders. Examples of delirium are delirium due to substance intoxication or substance withdrawal, delirium due to multiple etiologies and delirium NOS (not otherwise specified). Examples of dementia are: dementia of the Alzheimer's type with early onset which can be uncomplicated or with delirium, delusions or depressed mood; dementia of the Alzheimer's type, with late onset, which can be uncomplicated or with delirium, delusions or depressed mood; vascular dementia which can be uncomplicated or with delirium, delusions or depressed mood; dementia due to HIV disease; dementia due to head trauma; dementia due to Parkinson's disease; dementia due to Huntington's disease; dementia due to Pick's disease; dementia due to Creutzfeld-Jakob disease; dementia which is substance-induced persisting or due to multiple etiologies; and dementia NOS. Examples of amnestic disorders are amnestic disorder due to a particular medical condition or which is substance-induced persisting or which is amnestic disorder NOS. In particular the compounds of formula (I) may be of use in conditions which require cognition enhancement.

Where the compounds of the present invention are selective ligands for $GABA_A$ $\alpha$2 or $\alpha$3 subtype receptors they may be used in the treatment and/or prevention of a variety of disorders of the central nervous system. Such disorders include anxiety disorders, such as panic disorder with or without agoraphobia, agoraphobia without history of panic disorder, animal and other phobias including social phobias, obsessive-compulsive disorder, stress disorders including post-traumatic and acute stress disorder, and generalized or substance-induced anxiety disorder; neuroses; convulsions; migraine; and depressive or bipolar disorders, for example single-episode or recurrent major depressive disorder, dysthymic disorder, bipolar I and bipolar II manic disorders, and cyclothymic disorder.

The present invention also provides the use of a compound of formula (I) or a pharmaceutically acceptable salt thereof for the manufacture of a medicament for the treatment or prevention of a condition requiring the administration of a ligand selective for $GABA_A$ receptors containing the $\alpha$5 subunit, in particular for conditions requiring cognition enhancement such as Alzheimer's disease.

There is also disclosed a method of treatment or prevention of a condition associated with $GABA_A$ receptors containing the $\alpha$5 subunit which comprises administering to a subject suffering from or prone to such a condition a therapeutically or prophylactically effective amount of a compound of formula (I) or a pharmaceutically acceptable salt thereof. In particular there is disclosed the treatment and prevention of conditions which require the administration of a cognition enhancing agent, such as Alzheimer's disease.

As used herein, the expression "$C_{1-6}$alkyl" includes methyl and ethyl groups, and straight-chained and branched propyl, butyl, pentyl and hexyl groups. Particular alkyl groups are methyl, ethyl, n-propyl, isopropyl and t-butyl. Derived expressions such as "$C_{2-6}$alkenyl", "$C_{2-6}$alkynyl", "$C_{1-4}$alkyl", "$C_{2-4}$alkenyl" and "$C_{2-4}$alkynyl" are to be construed in an analogous manner.

The expression "$C_{3-6}$cycloalkyl" includes cyclopropyl, cyclobutyl, cyclopentyl and cyclohexyl groups. "$C_{5-6}$cycloalkenyl", "$C_{3-8}$cycloalkyl" and "$C_{5-7}$cycloalkyl" are to be construed analogously.

Suitable 5- and 6-membered heteroaromatic rings include pyridinyl, pyridazinyl, pyrimidinyl, pyrazinyl, furyl, thienyl, pyrrolyl, pyrazolyl, oxazolyl, isoxazolyl, isothiazolyl, imidazolyl, tetrazolyl, oxadiazolyl and thiadiazolyl groups. These rings also include thiazolyl and triazolyl groups.

The term "halogen" as used herein includes fluorine, chlorine, bromine and iodine, especially fluorine, chlorine and bromine.

The expression "arylC$_{1-6}$alkyl" as used herein includes benzyl, phenylethyl, phenylpropyl and naphthylmethyl. "ArylC$_{2-6}$alkenyl" and "arylC$_{2-6}$alkynyl" should be construed in an analogous fashion.

Typical aryl groups include phenyl and naphthyl. Preferably the aryl is phenyl.

For use in medicine, the salts of the compounds of formula (I) will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

Where the compounds of formula (I) have at least one asymmetric centre, they may accordingly exist as enantiomers. Where the compounds of formula (I) possess two or more asymmetric centres, they may additionally exist as diastereoisomers. It is to be understood that all such isomers and mixtures thereof in any proportion are encompassed within the scope of the present invention.

The present invention also provides a novel compound of formula (I) or a pharmaceutically acceptable salt thereof as defined above. The skilled person will appreciate that the alternative and preferred embodiments of these compounds in the pharmaceutical compositions described above are also alternative and preferred embodiments of the novel compounds of formula (I) provided by the present invention.

Aptly novel compounds of this invention include those wherein R$^2$ and R$^3$ are not 6-position gem-dimethyl.

Aptly novel compounds of this invention include those wherein p is 1 or 2.

Precursors of compounds of formula I, namely compounds of formula VII:

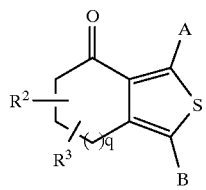

(VII)

wherein A, B, R$^2$, R$^3$ and q are as defined above, can be obtained by:

(i) reacting a compound of formula II:

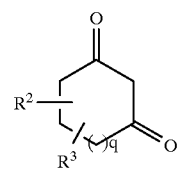

(II)

in which R$^2$, R$^3$ and q are as defined above, with NaH, then with CS$_2$, then with a compound of formula III and then with a compound of formula IV:

HalR$^1$ (III)

Hal'CH$_2$R$^{15}$ (IV)

in which R$^1$ is as defined above, Hal is a halogen atom such as iodine, Hal' is a halogen atom such as bromine or chlorine and R$^{15}$ is CN, COH C(O)C$_{1-6}$alkyl or CO$_2$C$_{1-6}$alkyl to produce a compound of formula VI:

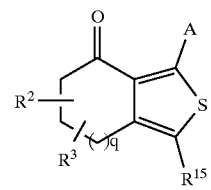

(VI)

in which A is S(O)$_p$R$^1$, p is zero and R$^1$, R$^2$, R$^3$, R$^{15}$ and q are as defined above and when R$^{15}$ is CO$_2$C$_{1-6}$alkyl optionally converting it by hydrolysis to a group of formula CO$_2$H and optionally decarboxylating this group to leave a hydrogen atom and optionally converting the hydrogen atom to a bromine atom by reacting with a brominating agent such as N-bromo succinimide or copper (I) bromide; and (ii) converting the group R$^{15}$ to a group B as defined above by standard techniques to obtain a compound of formula VII;

(iii) optionally oxidising the compound of formula VI or the compound of formula VII thus obtained to a compound of formula VI or VII in which p is 1 or 2, for example by using a stoichiometric quantity of mCPBA, generally in a solvent such as CH$_2$C$_2$:dioxan with cooling to about −78° C.; and (iv) optionally converting the compound of formula VI or VII, as the case may be, to a compound of formula VI or VII in which A is other than S(O)$_p$R$^1$ by standard techniques.

Step (i) is generally carried out in a solvent such as DMF and at about 0° C. to about room temperature.

Illustrative examples of conversions of the group R$^{15}$ to a group B are as follows; the skilled worker would have no difficulty in adapting these methods or in using other standard techniques to produce compounds in which B is other than as illustrated here: when R$^{15}$ is CN it can be converted to: a tetrazole using, for example, sodium azide, a thiazole using H$_2$S followed by HC(O)CH$_2$Cl; and a triazole using formyl hydrazine; when R$^{15}$ is CO$_2$H it can be converted to an oxadiazole by using: carbonyldiimidazole and an amide oxime; or hydrazine and formic acid; when R$^{15}$ is C(O)CH$_3$ it can be converted to an isoxazole using EtOC(O)H and NH$_2$OH.HCl.

Alternatively the group B can replace the group $R^{15}$ when the latter is bromine by a Stille reaction using the appropriate trialkyltin derivative and a catalyst such as dichlorobis(triphenylphosphine)palladium(II) or palladium tetrakisphenylphosphine or by a Suzuki reaction using the appropriate boronic acid derivative.

Further, when $R^{15}$ is $CO_2H$ it can be converted to a group B of formula $C(O)NR^{10}R^{11}$ by reacting with a compound of formula IX:

$$HNR^{10}R^{11} \qquad (IX)$$

wherein $R^{10}$ and $R^{11}$ are as defined above, generally in the presence of an acylation catalyst such as 4-dimethylamine pyridine and a coupling agent such as 1-(3-dimethylaminopropyl)-3-ethylcarbodiimide hydrochloride for about 18 h in a solvent such as DCM.

Further details of the above reactions can be found, for example, in Comprehensive Organic Syntheses, ed. B. M. Trost, Pergamon Press, Oxford.

Compounds of formula VI or VII in which A is SRI can be obtained by reacting ia compound of formula VI or VII in which A is $S(O)_pR^1$ where p is one or two and $R^1$ is as defined above with a thiol in the presence of a base.

Compounds of formula VI or VII in which A is $C_{1-6}$alkyl, $C_{2-6}$alkenyl, $C_{2-6}$alkynyl or $C_{3-6}$cycloalkyl can be obtained by reacting a compound of formula VI or VII in which A is $S(O)_pR$ where p is zero or two with an appropriate Grignard reagent.

Compounds of formula VI or VII in which A is $OR^1$ can be obtained by reacting a compound of formula VI or VII in which A is $S(O)_pR^1$ and p is one or two with an alcohol in the presence of a strong base.

Compounds of formula I or VI in which A is $NR^1R^{14}$ can be obtained by reacting a compound of formula I or VI in which A is $S(O)_pR^1$ and p is one or two with an amine.

It will be understood that the above transformations of $S(O)_pR^1$ are illustrative and other standard techniques known to the skilled person may alternatively be used. The above reactions are illustrated in the Examples.

Compounds of formula VI in which $R^{15}$ is CN, Br or $C(O)CH_3$, p is zero, $R^1$ is $CH_3$ and $R^2$ and $R^3$ are 6,6-dimethyl are commercially available.

The compound of formula VI in which p is zero, $R^1$ is $CH_3$, $R^2$ and $R^3$ are 6,6-dimethyl and $R^{15}$ is bromo can be prepared from

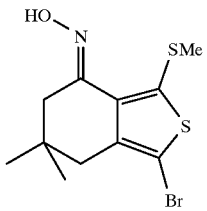

which is commercially available by heating the above compound with 1M HCl in THF and methanol.

The compound of formula VII in which A is methylthio, B ispyrazol-3-yl, $R^2$ and $R^3$ are 6,6-dimethyl and q is 1 is commercially available; it can also be made by the methods disclosed herein.

Compounds of formulae II, III, IV and IX are known in the art or can be made by known methods from known starting materials.

The present invention also provides a process for producing a compound of formula I which comprises:

(i) reacting a compound of formula VII as defined above with a strong base such as NaH and $EtO_2CCHO$ generally in a solvent such as THF to produce a compound of formula VIII:

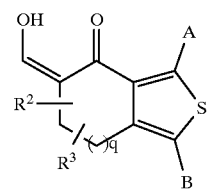

(VIII)

wherein A, B, $R^2$ $R^3$ and q are as hereinbefore defined; and (ii) reacting the compound of formula VIII with $NH_2OH$, in the form of its hydrochloride salt generally in a solvent such as ethanol generally at reflux for about 2 h to produce the compound of formula I; and (iii) optionally converting the compound of formula I thus obtained into another compound of formula I by standard techniques; and (iv) optionally converting the compound of formula I if in free base form into a pharmaceutically acceptable salt or if in salt form into free base or another pharmaceutically acceptable salt.

The following Examples illustrate pharmaceutical compositions according to the invention.

COMPOSITION EXAMPLE 1A

Tablets Containing 1–25 mg of Compound

|  | Amount mg | | |
| --- | --- | --- | --- |
| Active Ingredients(s) | 1.0 | 2.0 | 25.0 |
| Microcrystalline cellulose | 20.0 | 20.0 | 20.0 |
| Modified food corn starch | 20.0 | 20.0 | 20.0 |
| Lactose | 58.5 | 57.5 | 34.5 |
| Magnesium Stearate | 0.5 | 0.5 | 0.5 |

COMPOSITION EXAMPLE 1B

Tablets Containing 26–100 mg of Compound

|  | Amount mg | | |
| --- | --- | --- | --- |
| Active Ingredients(s) | 26.0 | 50.0 | 100.0 |
| Microcrystalline cellulose | 80.0 | 80.0 | 80.0 |
| Modified food corn starch | 80.0 | 80.0 | 80.0 |
| Lactose | 213.5 | 189.5 | 139.5 |
| Magnesium Stearate | 0.5 | 0.5 | 0.5 |

The active ingredient(s), cellulose, lactose and a portion of the corn starch are mixed and granulated with 10% corn starch paste. The resulting granulation is sieved, dried and blended with the remainder of the corn starch and the magnesium stearate. The resulting granulation is then compressed into tablets containing 1.0 mg, 2.0 mg, 25.0 mg, 26.0 mg, 50.0 mg and 100 mg of the active compound per tablet.

COMPOSITION EXAMPLE 2

Parenteral Injection

| | Amount |
|---|---|
| Active Ingredient(s) | 1 to 100 mg |
| Citric Acid Monohydrate | 0.75 mg |
| Sodium Phosphate | 4.5 mg |
| Sodium Chloride | 9 mg |
| Water for injection | to 10 ml |

The sodium phosphate, citric acid monohydrate and sodium chloride are dissolved in a portion of the water. The active ingredient(s) is (are) dissolved or suspended in the solution and made up to volume.

COMPOSITION EXAMPLE 3

Topical Formulation

| | Amount |
|---|---|
| Active Ingredient(s) | 1–10 g |
| Emulsifying Wax | 30 g |
| Liquid paraffin | 20 g |
| White Soft Paraffin | to 100 g |

The white soft paraffin is heated until molten. The liquid paraffin and emulsifying wax are incorporated and stirred until dissolved. The active ingredient(s) is (are) is added and stirring continued until dispersed. The mixture is then cooled until solid.

The following Examples illustrate the compounds of the present invention.

The compounds in accordance with this invention potently inhibit the binding of [$^3$H]-flumazenil to the benzodiazepine binding site of human GABA$_A$ receptors containing the α5 subunit stably expressed in Ltk cells.

Reagents

Phosphate buffered saline (PBS).

Assay buffer: 10 mM KH$_2$PO$_4$, 100 mM KCl, pH 7.4 at room temperature.

[$^3$H]-Flumazenil (18 nM for α1β3γ2 cells; 18 nM for α2β3γ2 cells; 10 nM for α3β3γ2 cells; 10 nM for α5β3γ2 cells) in assay buffer.

Flunitrazepam 100 μM in assay buffer.

Cells resuspended in assay buffer (1 tray to 10 ml).

Harvesting Cells

Supernatant is removed from cells. PBS (approximately 20 ml) is added. The cells are scraped and placed in a 50 ml centrifuge tube. The procedure is repeated with a further 10 ml of PBS to ensure that most of the cells are removed. The cells are pelleted by centrifuging for 20 min at 3000 rpm in a benchtop centrifuge, and then frozen if desired. The pellets are resuspended in 10 ml of buffer per tray (25 cm×25 cm) of cells.

Assay

Can be carried out in deep 96-well plates or in tubes. Each tube contains:

300 μl of assay buffer.

50 μl of [$^3$H]-flumazenil (final concentration for (α1β3γ2: 1.8 nM; for α2β3γ2: 1.8 nM; for α3β3γ2: 1.0 nM; for α5β3γ2: 1.0 nM).

50 μl of buffer or solvent carrier (e.g. 10% DMSO) if compounds are dissolved in 10% DMSO (total); test compound or flunitrazepam (to determine non-specific binding), 10 μM final concentration.

100 μl of cells.

Assays are incubated for 1 hour at 40° C., then filtered using either a Tomtec or Brandel cell harvester onto GF/B filters followed by 3×3 ml washes with ice cold assay buffer. Filters are dried and counted by liquid scintillation counting. Expected values for total binding are 3000–4000 dpm for total counts and less than 200 dpm for non-specific binding if using liquid scintillation counting, or 1500–2000 dpm for total counts and less than 200 dpm for non-specific binding if counting with meltilex solid scintillant. Binding parameters are determined by non-linear least squares regression analysis, from which the inhibition constant K$_i$ can be calculated for each test compound.

The compounds of the accompanying Examples were tested in the above assay, and all were found to possess a K$_i$ value for displacement of [$^3$H]Ro 15-1788 from the α5 subunit of the human GABA$_A$ receptor of 300 nM or less, preferably of 100 nM or less, and more particularly of 50 nM or less.

The following Examples illustrate the present invention.

EXAMPLE 1

(4,4-Dimethyl-8-methylthio-4,5-dihydrothieno[3,4-g]-1,2-benzisoxazol-6-yl)(pyrrolidin-1-yl)methanone Step 1: 6,6-Dimethyl-3-methylthio-1-(pyrrolidin-1-ylcarbonyl)-4,5,6,7-tetrahydrobenzo[c]thiophen-4-one To a stirred solution of 6,6-dimethyl-3-methylthio-4-oxo-4,5,6,7-tetrahydrobenzo[c]thiophene-1-carboxylic acid (1.0 g, 3.7 mmol), 4-dimethylaminopyridine (0.75 g, 6.1 mmol) and 1-(3-dimethylaminopropyl)-3-ethylcarbodiimide hydrochloride (1.15 g, 6 mmol) in DCM (30 mL) was added pyrrolidine (0.34 mL, 4.1 mmol). The mixture was stirred for 18 h then the solution was evaporated and the residue partitioned between EtOAc (20 mL) and water (20 mL). The organic layer was separated, washed with 1M HCl (2×20 mL) and sat. K$_2$CO$_3$ (20 mL). The organic layer was separated, dried (MgSO$_4$) and evaporated. The residue was triturated with hexane/ether to afford the title amide (905 mg, 76%) as a colourless solid. mp 153–155° C. C$_{16}$H$_{21}$NO$_2$S$_2$ requires: C, 59.41; H, 6.54; N, 4.33%. Found: C, 59.70; H, 6.73; N, 4.77%, $^1$H NMR (360 MHz, CDCl$_3$) δ1.05 (6H, s), 1.94–2.04 (4H, m), 2.40 (2H, s), 2.59 (3H, s), 2.84 (2H, s), 3.59–3.62 (4H, m). MS (ES$^+$) 324 (M+1).

Step 2: 6,6-Dimethyl-5-hydroxymethylene-3-methylthio-1-(pyrrolidin-1-ylcarbonyl)-4,5,6,7-tetrahydrobenzo[c]thiophen-4-one To a suspension of NaH (76 mg of a 60% dispension in oil, 1.9 mmol) in THF (5 ml,) was added ethyl formate (0.38 mL, 4.7 mmol) at 0° C. After stirring for 10 min a solution of 6,6-dimethyl-3-methylthio-1-(pyrrolidin-1-ylcarbonyl)-4,5,6,7-tetrahydrobenzo[c]thiophen-4-one (305 mg, 0.94 mmol) in THF (7 mL) was added. The cooling bath was removed and the mixture stirred at room temperature for 18 h. After this time MeOH (0.5 mL) followed by water (0.5 mL) were added and the mixture stirred for 10 min. The solvents were removed in vacuo and the residue dissolved in water. The mixture was acidified to pH1 using 1 M HCl and the resultant solid collected by filtration. The solid was partitioned between EtOAc (20 mL) and water (20 mL). The organic layer was separated, dried (Na$_2$SO$_4$) and evaporated. The residue was chromatographed on silica gel, eluting with EtOAc: DCM (10:90), to give the title compound (173 mg, 52%) as a pale yellow oil. $^1$H NMR (250 MHz, CDCl$_3$)

δ1.18 (6H, s),1.93–1.99 (4H, m), 2.63 (3H, s), 2.82 (2H, s), 3.56–3.70 (4H, m), 7.56 (1H, d, J=10.4 Hz), 14.63 (1H, d J=10.4 Hz).

Step 3: (4,4-Dimethyl-8-methylthio-4,5-dihydrothieno[3,4-g]-1,2-benzisoxazol-6-yl)(pyrrolidin-1-yl)methanone To a solution of 6,6-dimethyl-5-hydroxymethylene-3-methylthio-1-(pyrrolidin-1-ylcarbonyl)-4,5,6,7-tetrahydrobenzo[c]thiophen-4-one (173 mg, 0.49 mmol) in EtOH (4 mL) and water (0.7 mL) was added hydroxylamine hydrochloride (38 mg, 0.54 mmol). The solution was heated at reflux for 2 h then cooled to room temperature and the solvent evaporated. The residue was partitioned between EtOAc (20 mL) and water (20 mL), the organic layer separated, dried ($Na_2SO_4$) and evaporated. The residue was triturated with hexane/$Et_2O$ and the resultant yellow solid (131 mg, 77%) collected by filtration. mp 114–116° C. $C_{17}H_2ON_{20}N_2S_2O_2$.0.1($H_2O$) requires: C, 58.29; H, 5.81; N, 8.00%. Found: C, 58.05; H, 5.59; N, 7.65%. $^1$H NMR (360 MHz, $CDCl_3$) δ1.26 (6H, s), 1.94–1.98 (4H, m), 2.63 (3H, s), 2.90 (2H, s), 3.56–3.67 (4H, m), 8.20 (1H, s). MS ($ES^+$) 349 (M+1).

EXAMPLE 2

(Dimethylamino)(4,4-dimethyl-8-methylthio-4,5-dihydrothieno[3,4-g]-1,2-benzisoxazol-6-yl) methanone Step 1: 6,6-Dimethyl-1-(dimethylaminocarbonyl)-3-methylthio-4,5,6,7-tetrahydrobenzo[c]thiophen-4-one In the same way as Example 1, Step 1, using dimethylamine, the title compound (764 mg, 70%) was isolated as a cream solid. mp 135–136° C. $C_{14}H_{19}NO_2S_2$ requires: C, 56.53; H, 6.44; N, 4.71%. Found: C, 56.37; H, 6.31; N, 4.57%. $^1$H NMR (250 MHz, $CDCl_3$) δ1.05 (6H, s), 2.40 (2H, s), 2.59 (3H, s), 2.67 (2H, s), 3.10 (4H, s). MS ($ES^+$) 298 (M+1).

Step 2: 6,6-Dimethyl-1-(dimethylaminocarbonyl)-5-hydroxymethylene-3-methylthio-4,5,6,7-tetrahydrobenzo[c]thiophen-4-one In the same as that described in Example 1, Step 2, using 6,6-dimethyl-1-(dimethylaminocarbonyl)-3-methylthio-4,5,6,7-tetrahydrobenzo[c]thiophen-4-one, the title compound (205 mg, 56%) was isolated as a pale yellow solid. $^1$H NMR (250 MHz, $CDCl_3$) δ1.18 (6H, s), 2.64 (3H, s), 2.65 (2H, s), 3.09 (6H, s), 7.57 (1H, d, J=10.4 Hz), 14.65 (1H, d, J=10.4 Hz).

Step 3: (4,4-Dimethyl-8-methylthio-4,5-dihydrothieno[3,4-g]-1,2-benzisoxazol-6-yl)dimethylaminomethanone In the same way as described in Example 1, Step 3, using 6,6-dimethyl-1-(dimethylaminocarbonyl)-5-hydroxymethylene-3-methylthio-4,5,6,7-tetrahydrobenzo[c]thiophen-4-one, the isoxazole (119 mg, 59%) was isolated as a pale yellow solid. mp 113–115° C. $C_{15}H_{19}NO_3S_2$ requires: C, 55.87; H, 5.63; N, 8.69%. Found: C, 55.49; H, 5.62; N, 8.58%. $^1$H NMR (360 MHz, $CDCl_3$) δ1.27 (6H, s), 2.64 (3H, s), 2.73 (3H, s), 3.10 (6H, s), 8.20 (1H, s). MS ($ES^+$) 323 (M+1).

EXAMPLE 3

(4,4-Dimethyl-8-methylthio-4,5-dihydrothieno[3,4-g]-1,2-benzisoxazol-6-yl)([N-methyl]cyclohexylamino)methanone Step 1: 6,6-Dimethyl-1-[(N-methyl)cyclohexylaminocarbonyl]-3-methylthio-4,5,6,7-tetrahydrobenzo[c]thiophen-4-one In the same way as described in Example 1, Step 1, using (N-methyl)cyclohexylamine, the title amide (1.06 g, 78%) was isolated as a colourless solid. mp 161–163° C. $C_{19}H_{27}NO_2S_2$.0.2($H_2O$) requires: C, 61.82; H, 7.48; N, 3.79%. Found: C, 61.89; H, 7.41; N, 3.67%. $^1$H NMR (360 MHz, $CDCl_3$) δ1.08 (6H, s), 1.23–1.40 (2H, m), 1.49–1.90 (8H, m), 2.39 (2H, s), 2.58 (3H, s), 2.64 (2H, s), 2.94 (3H, s), 3.90–4.10 (1H, m). MS ($ES^+$) 366 (M+1).

Step 2: 6,6-Dimethyl-5-hydroxymethylene-1-[(N-methyl)cyclohexylaminocarbonyl]-3-methylthio-4,5,6,7-tetrahydrobenzo[c]thiophen-4-one In the same way as that described in Example 1, Step 2, using 6,6-dimethyl-1-[(N-methyl)cyclohexylaminocarbonyl]-3-methylthio-4,5,6,7-tetrahydrobenzo[c]thiophen-4-one, the title compound (47 mg, 11%) was isolated as a pale yellow solid. $^1$H NMR (360 MHz, $CDCl_3$) δ1.18 (6H, s), 1.22–1.44 (3H, m), 1.48–1.61 (2H, m), 1.64–1.78 (3H, m), 1.79–1.90 (2H, m), is 2.62 (2H, s), 2.63 (3H, s), 2.93 (3H, s), 3.76–4.18 (1H, m), 7.58 (1H, d, J=10.4 Hz), 14.67 (1H, d, J=10.4 Hz). MS ($ES^+$) 394 (M+1).

Step 3: (4,4-Dimethyl-8-methylthio-4,5-dihydrothieno[3,4-g]-1,2-benzisoxazol-6-yl)([N-methyl]cyclohexylamino) methanone In the same way as that described in Example 1, Step 3, using 6,6-dimethyl-5-hydroxymethylene-1-[(N-methyl)cyclohexylaminocarbonyl]-3-methylthio-4,5,6,7-tetrahydrobenzo[c]thiophen-4-one, the isoxazole (31 mg; 66%) was isolated as a pale yellow solid. mp 150–153° C. $C_{20}H_{26}N_2O_2S_2$ requires: C, 61.51; H, 6.71; N, 7.17%. Found: C, 61.69; H, 6.77; N, 7.25%. $^1$H NMR (360 MHz, $CDCl_3$) δ1.05–1.19 (1H, m), 1.20–1.42 (8H, m), 1.48–1.61 (2H, m), 1.62–1.78 (3H, m), 1.79–1.90 (2H, m), 2.63 (3H, s), 2.70 (2H, s), 2.94 (3H, s), 3.78–4.10 (1H, m), 8.19 (1H, s). MS ($ES^+$) 391 (M+1).

EXAMPLE 4

(4,4-Dimethyl-8-ethoxy-4,5-dihydrothieno[3,4-g]-1,2-benzisoxazol-6-yl)(pyrrolidin-1-yl)methanone Step 1: 6-6,Dimethyl-3-ethoxy-4-oxo-4,5,6,7-tetrahydrobenzo[c]thiophene-1-carboxylic acid A solution of ethyl 6,6-dimethyl-3-methanesulphonyl-4-oxo-4,5,6,7-tetrahydrobenzo[c]thiophene-1-carboxylate (2.4 g, 7.3 mmol) in EtOH (20 mL) was treated with sodium (0.35 g, 15 mmol) and the mixture heated at reflux for 4 h. The solvent was removed it vacuo and the residue partitioned between EtOAc (50 mL) and water (50 mL). The aqueous layer was separated, acidified to pH3 using 1M HCl, and extracted with EtOAc (2×30 ml). The combined organic layers were dried ($MgSO_4$) and evaporated. The residue was triturated with hexane/$Et_2O$ and the resultant acid (214 mg, 11%) isolated as a beige solid. mp 188–190° C. $C_{13}H_{16}O_4S$ requires: C, 58.19; H, 6.01%. Calc: C, 58.06; H, 5.97% $^1$H NMR (250 MHz, $CDCl_3$) δ1.07 (6H, s), 1.61 (3H, t, J=7.0 Hz), 2.37 (2H, s), 3.08 (2H, s), 4.36 (2H, q, J=7.0 Hz). MS ($ES^+$) 269 (M+1).

Step 2: 6,6-Dimethyl-3-ethoxy-1-(pyrrolidin-1-ylcarbonyl)-4,5,6,7-tetrahydrobenzo[c]thiophen-4-one In the same way as described in Example 1, Step 1, using 6,6-dimethyl-3-ethoxy-4-oxo-4,5,6,7-tetrahydrobenzo[c]thiophene-1-carboxylic acid, the title amide (310 mg, 64%) was isolated as a beige solid. $^1$H NMR (360 MHz, $CDCl_3$) δ1.03 (6H, s), 1.56 (3H, t, J=7.0 Hz), 1.93–1.97 (4H, m), 2.34 (2H, s). 2.80 (2H, s), 3.57–3.60 (4H, m), 4.28 (2H, q, J=7.0 Hz). MS ($ES^+$) 322 (M+1).

Step 3: 6,6-Dimethyl-3-ethoxy-5-hydroxymethylene-1-(pyrrolidin-1-ylcarbonyl)-4,5,6,7-tetrahydrobenzo[c]thiophen-4-one In the same way as described for Example 1, Step 2, using 6,6-dimethyl-3-ethoxy-1-(pyrrolidin-1-ylcarbonyl)-4,5,6,7- tetrahydrobenzo[c]thiophen-4-one, the title compound (101 mg, 30%) was isolated as a pale yellow solid. mp 140–142° C. $^1$H NMR (360 MHz, CDCl$_3$) δ1.18 (6H, s), 1.58 (3H, t, J=7.0 Hz), 1.92–1.96 (4H, m), 2.76 (2H, s), 3.56–3.59 (4H, m), 4.32 (2H, q, J=7.0 Hz), 7.72 (1H, d, J=9.4 Hz), 15.20 (1H, d, J=9.4 Hz). MS (ES$^+$) 350(M+1).

Step 4: (4,4-Dimethyl-8-ethoxy-4,5-dihydrothieno[3,4-g]-1,2-benzisoxazol-6-yl)(pyrrolidin-1-yl)methanone In the same way as described in Example 1, Step 3, using 6,6-dimethyl-3-et hoxy-5-hydroxymethylene-1-(pyrrolidin-1-ylcarbonyl)-4,5,6,7-tetrahydrobenzo[c]thiophen-4-one, the isoxazole (73 mg, 75%) was isolated as a yellow solid. mp 123–126° C. $C_{18}H_{22}N_2O_3S$ requires C, 62.40; H, 6.40; N, 8.09%. Found: C, 62.06; H, 6.25; N, 7.90%. $^1$H NMR (250 MHz, CDCl$_3$) δ1.25 (6H, s), 1.54 (3H, t, J=7.0 Hz), 1.92–1.98 (4H, m), 2.90 (2H, s), 3.58–3.64 (4H, m), 4.28 (2H, q), 8.15 (1H, s). MS (ES$^+$) 347 (M+1).

EXAMPLE 5

(4,4-Dimethyl-8-methylthio-4,5-dihydrothieno[3,4-g]-1,2-benzisoxazol-6-yl)(homopiperidin-1-yl)methanone Step 1: 6,6-Dimethyl-1-(homopiperidin-1-ylcarbonyl)-3-methylthio-4,5,6,7-tetrahydrobenzo[c]thiophen-4-one In the same way as described in Example 1, Step 1, using hexamethyleneimine the title compound (1.0 g, 85%) was isolated as a colourless solid. mp 168–170° C. $C_{18}H_{25}NO_2S_2$ requires: C, 61.50; H, 7.17; N, 3.98%. Found: C, 61.81; H, 7.17; N, 3.83%. $^1$H NMR (360 MHz, CDCl$_3$) δ1.04 (6H, s), 1.58–1.68 (4H, m), 1.70–1.80 (4H, m), 2.39 (2H, s), 2.58 (3H, s), 2.67 (2H, s), 3.56–3.65 (4H, m). MS (ES$^+$) 352 (M+1).

Step 2: 6,6-Dimethyl-1-(homopiperidin-1-ylcarbonyl)-5-hydroxymethylene-3-methylthio-4,5,6,7-tetrahydrobenzo[c]thiophen-4-one In the same say as described in Example 1, Step 2, using 6,6-dimethyl-1-(homopiperidin-1-ylcarbonyl)-3-methylthio-4,5,6,7-tetrahydrobenzo[c]thiophen-4-one, the title compound (0.31 mg, 57%) was isolated as a yellow solid. $^1$H NMR (360 MHz, CDCl$_3$) δ1.18 (6H, s), 1.52–1.81 (8H, m), 2.63 (3H, s), 2.65 (2H, s), 3.52–3.63 (4H, m), 7.57 (1H, d, J=10.3 Hz), 14.65 (1H, d, J=10.3 Hz). MS (ES$^+$) 380 (M+1).

Step 3: (4,4-Dimethyl-8-methylthio-4,5-dihydrothieno[3,4-g]-1,2-benzisoxazol-6-yl)(homopiperidin-1-yl)methanone In the same way as described in Example 1, Step 3, using 6,6-dimethyl-1-(homopiperidin-1-ylcarbonyl)-3-methylthio-4,5,6,7-tetrahydrobenzo[c]thiophen-4-one, the isoxazole (205 mg, 67%) was isolated as a colourless solid. mp 99–101° C. $C_{19}H_{24}N_2O_2S_2$ requires: C, 61.50; H, 7.17; N, 3.98%. found: C, 61.81; H, 7.17; N. 3.83%. $^1$H NMR (360 MHz, CDCl$_3$) δ1.26 (6H, s), 1.59–1.90 (8H, m), 2.63 (3H, s), 2.73 (2H, s), 3.52–3.68 (4H, m), 8.19 (1H, s). MS (ES$^+$) 377 (M+1).

EXAMPLE 6

(4,4-Dimethyl-8-isopropylthio-4,5-dihydrothieno[3,4-g]-1,2-benzisoxazol-6-yl)(pyrrolidin-1-yl)methanone Step 1: 6-6-Dimethyl-3-methanesulphonyl-1-(pyrrolidin-1-ylcarbonyl)-4,5,6,7-tetrahydrobenzo[c]thiophen-4-one To a stirred solution of 6,6-dimethyl-3-methylthio-1-(pyrrolidin-1-ylcarbonyl)-4,5,6,7-tetrahydrobenzo[c]thiophen-4-one (5.0 g, 16 mmol) in DCM (400 mL) was added meta-chloroperoxybenzoic acid (11.4 g, (70% tech.), 46 mmol) and the mixture stirred at room temperature for 18 h. The solution was washed with Na$_2$CO$_3$ (sat., 3×200 mL), the organic layer separated, dried (Na$_2$SO$_4$) and evaporated. The residue was triturated with ether and the sulphone (4.88 g, 89%) collected by filtration and isolated as a colourless solid. mp 161° C. $C_{16}H_{21}NO_4S_2$ requires: C, 54.06; H, 5.95; N, 3.94%. Found: C, 53.76; H, 5.78; N, 3.89%. $^1$H NMR (250 MHz, CDCl$_3$) δ1.10 (6H, s), 1.97–2.03 (4H, m), 2.53 (2H, s), 2.90 (2H, s), 3.47–3.78 (7H, m). MS (ES$^+$) 356 (M+1).

Step 2: 6,6-Dimethyl-3-isopropylthio-1-(pyrrolidin-1-ylcarbonyl)-4,5,6,7-tetrahydrobenzo[c]thiophen-4-one To a suspension of 6,6-dimethyl-3-methanesulphonyl-1-(pyrrolidin-1-ylcarbonyl)-4,5,6,7-tetrahydrobenzo[c]thiophen-4-one (400 mg, 1.1 mmol) in EtOH (15 mL) was added NaOH (0.75 mL of a 3N aqueous solution, 2.25 mmol) followed by 2-propanethiol (0.21 mL, 2.25 mmol). The mixture was stirred at room temperature for 3 h then the solvent evaporated in vacuo and the residue partitioned between EtOAc (20 mL) and water (30 mL). The organic phase was separated, dried (Na$_2$SO$_4$) and evaporated. The residue was triturated with hexane to afford the title amide (175 mg, 44%) as a colourless solid. $C_{18}H_{25}NO_2S_2$ requires: C, 61.50; H, 7.17; N, 3.98%. Found: C, 61.42; H, 7.12; N, 3.92%. $^1$H NMR (250 MHz, CDCl$_3$) δ1.04 (6H, s), 1.48 (6H, d, J=6.6 Hz), 1.93–1.99 (4H, m), 2.40 (2H, s), 2.82 (2H, s), 3.49 (1H, septet, J=6.6 Hz), 3.59–3.65 (4H, m). MS (ES$^+$) 352 (M+1).

Step 3: 6,6-Dimethyl-5-hydroxymethylene-3-isopropylthio-1-(pyrrolidin-1-ylcarbonyl)-4,5,6,7-tetrahydrobenzo[c]thiophen-4-one In the same way as described in Example 1, Step 2, using 6,6-dimethyl-3-isopropylthio-1-(pyrrolidin-1-ylcarbonyl)-4,5,6,7-tetrahydrobenzo[c]thiophen-4-one, the title compound (110 mg, 61%) was isolated as a gum. $^1$H NMR (360 MHz, CDCl$_3$) δ1.18 (6H, s), 1.50 (6H, d, J=6.7 Hz), 1.93–1.98 (4H, m), 2.79 (2H, s), 3.54–3.65 (5H, m), 7.60 (1H, d, J=10.2 Hz), 14.72 (1H, d, J=10.2 Hz). MS (ES$^+$) 380 (M+1).

Step 4: (4,4-Dimethyl-8-isopropylthio-4,5-dihydrothieno[3,4-g]-1,2-benzisoxazol-6-yl)(pyrrolidin-1-yl)methanone In the same way as described in Example 1, Step 3 using 6,6-dimethyl-5-hydroxymethylene-3-isopropylthio-1-(pyrrolidin-1-ylcarbonyl)-4,5,6,7-tetrahydrobenzo[c]thiophen-4-one, the isoxazole (40 mg, 37%) was isolated as a cream solid. mp 88–91° C. $C_{19}H_{24}N_2O_2S_2$ requires: C, 60.61; H, 6.42; N, 7.44%. Found: C, 60.80; H, 6.36; N, 7.27%. $^1$H NMR (360 MHz, CDCl$_3$) δ1.26 (6H, s), 1.34 (6H, d, J=6.7 Hz), 1.94–1.99 (4H, m), 2.90 (2H, s), 3.48 (1H, septet, J=6.7 Hz), 3.52–3.68 (4H, m), 8.20 (1H, s). MS (ES$^+$) 377 (M+1).

EXAMPLE 7

(4,4-Dimethyl-8-methylthio-4,5-dihydrothieno[3,4-g]-1,2-benzisoxazol-6-yl)(morpholin-4-yl)methanone Step 1: 6,6-Dimethyl-3-methylthio-1-(morpholin-4-ylcarbonyl)-4,5,6,7-tetrahydrobenzo[c]thiophen-4-one In the same way as that described in Example 1, Step 1 using morpholine, the title amide (1.1 g, 87%) was isolated as a colourless solid. mp 168–169° C. $C_{16}H_{21}NO_3S_2$ requires: C, 56.61; H, 6.24; N, 4.13%. Found: C, 56.73; H, 6.06; N, 4.01%. $^1$H NMR (360 MHz, CDCl$_3$) δ1.05 (6H, s), 2.40 (2H, s), 2.59 (3H, s), 2.67 (2H, s), 3.64–3.67 (4H, m), 3.71–3.74 (4H, m). MS (ES$^+$) 340 (M+1).

Step 2: 6,6-Dimethyl-5-hydroxymethylene-3-methylthio-1-(morpholin-4-ylcarbonyl)-4,5,6,7-tetrahydrobenzo[c]thiophen-4-one In the same way as described in Example 1, Step 2, using 6,6-dimethyl-3-methylthio-1-(morpholin-4-ylcarbonyl)-4,5, 6,7-tetrahydrobenzo[c]thiophen-4-one, the title compound (90 mg, 28%) was isolated as an orange solid. $^1$H NMR (360 MHz, CDCl$_3$) δ1.18 (6H, s), 2.64 (3H, s), 2.65 (2H, s), 3.63–3.66 (4H, m), 3.70–3.73 (4H, m), 7.58 (1H, d, J=10.4 Hz), 14.63 (1H, d, J=10.4 Hz).

Step 3: (4,4-Dimethyl-8-methylthio-4,5-dihydrothieno[3,4-g]-1,2-benzisoxazol-6-yl)(morpholin-4-yl)methanone In the same way as described in Example 1, Step 3, using 6,6-dimethyl-5-hydroxymethylene-3-methylthio-1-(morpholin-4-ylcarbonyl)-4,5,6,7-tetrahydrobenzo[c]thiophen-4-one, the isoxazole (65 mg, 73%) was isolated as a colourless solid. mp 175–177° C. $C_{17}H_{20}N_2O_3S_2$ requires: C, 56.02; H, 5.53; N, 7.69%. Found: C, 56.18; H, 5.84; N, 7.77%. $^1$H NMR (250 MHz, CDCl$_3$) δ1.27 (6H, s), 2.64 (3H, s), 2.74 (2H, s), 3.64–3.75 (8H, m), 8.20 (1H, s). MS (ES$^+$) 365 (M+1).

EXAMPLE 8

(4,4-Dimethyl-8-methylthio-4,5-dihydro[2-$^{15}$N]-thieno[3.4-g]-1,2-benzisoxazol-6-yl) (4-methylpiperazin-1-yl)methanone Step 1: 6,6-Dimethyl-1-(4-methylpiperazin-1-ylcarbonyl)-3-methylthio-4,5,6,7-tetrahydrobenzo[c]thiophen-4-one In the same way as that described in Example 1, Step 1 using N-methylpiperazine, the title compound (0.5 g, 39%) was isolated as a colourless solid. mp 123–125° C. $C_{17}H_{24}N_2O_2S_2$ requires: C, 57.92; H, 6.86; N, 7.95%. Found: C, 58.12; H, 6.94; N, 7.84%. $^1$H NMR (250 MHz, CDCl$_3$) δ1.05 (6H, s), 2.33 (3H, s), 2.40 (2H, s), 2.41–2.46 (4H, m), 2.59 (3H, s), 2.66 (2H, s), 3.64–3.68 (4H, m). MS (ES$^+$) 353 (M+1).

Step 2: 6,6-Dimethyl-5-hydroxymethylene-1-(4-methylpiperazin-1-ylcarbonyl)-3-methylthio-4,5,6,7-tetrahydrobenzo[c]thiophen-4-one In the same way as described in Example 1, Step 2, using 6,6-dimethyl-1-(4-methylpiperazin-1-ylcarbonyl)-3-methylthio-4,5,6,7-tetrahydrobenzo[c]thiophen-4-one, the title compound (120 mg, 40%) was isolated as a yellow solid. $^1$H NMR (250 MHz, CDCl$_3$) δ1.18 (6H, s), 2.36 (2H, s), 2.42–2.58 (4H, m), 2.64 (3H, s), 3.61–3.79 (4H, m), 7.58 (1H, d, J=11.2 Hz), 14.62 (1H, d, J=11.2 Hz). MS (ES$^+$) 381 (M+1).

Step 3: (4,4-Dimethyl-8-methylthio-4,5-dihydro[2-$^{15}$N]-thieno[3,4-g]-1,2-benzisoxazol-6-yl)(4-methylpiperazin-1-yl)methanone In the same way as described in Example 1, Step 3, using 6,6-dimethyl-5-hydroxymethylene-1-(4-methylpiperazin-1-ylcarbonyl)-3-methylthio-4,5,6,7-tetrahydrobenzo[c]thiophen-4-one and $^{15}$N-hydroxylamine hydrochloride, the isoxazole (10 mg, 8%) was isolated as a colourless solid. $^1$H NMR (360 MHz, CDCl$_3$) δ1.26 (6H, s), 2.33 (3H, s), 2.42–2.46 (4H, m), 2.64 (3H, s), 2.73 (2H, s), 3.64–3.67 (4H, m), 8.19 (1H, d, J=14.4 Hz). MS (ES$^+$) 379 (M+1).

EXAMPLE 9

8-Methylthio-6-(thiazol-2-yl)-4 5-dihydrothieno[3,4-g]-1,2-benzisoxazole

Step 1: 8-Methylthio-4,5-dihydrothieno[3,4-g]-1,2-benzisoxazole-6-carbothioic acid amide Hydrogen sulphide was bubbled through a solution of 8-methylthio-4,5-dihydrothieno[3,4-g]-1,2-benzisoxazole-6-carbonitrile in pyridine (4 mL) and Et$_3$N (0.2 mL) for 15 min. The solution was allowed to stand at room temperature for 20 min then poured into water (30 ml) and stirred for 1 h. The resultant yellow solid was filtered, washed with water followed by hexane, then dried under vacuum. The thioamide (100 mg, 66%) was isolated as a yellow solid. mp 207–210° C. $^1$H NMR (360 MHz, CDCl$_3$) δ2.67 (3H, s), 2.79 (2H, t, J=7.3 Hz), 3.21 (2H, t, J=7.3 Hz), 8.00–8.21 (1H, brs), 8.19 (1H, s), 8.85 (1H, brs). MS (ES$^+$) 283 (M+1).

Step 2: 8-Methylthio-6-(thiazol-2-yl)-4,5-dihydrothieno[3,4-g]-1,2-benzisoxazole To a solution of the thioamide (100 mg, 0.35 mmol) in EtOH (5 mL) and THF (3 mL) was added chloroacetaldehyde (290 μL of a 50% (w/v) aqueous solution, 1.8 mmol) and the mixture heated at reflux for 36 h. The solution was then evaporated and the residue chromatographed on silica gel, eluting with hexane: EtOAc (2:1), to give the thiazole (18 mg, 17%) as a cream solid. mp 165–168° C. $C_{13}H_{10}N_2OS_3.0.2(H_2O)$ requires: C, 50.36; H, 3.38; N, 9.04%. Found: C, 50.20; H, 3.09; N, 8.74%. $^1$H NMR (360 MHz, CDCl$_3$) δ2.69 (3H, s), 2.88 (2H, t, J=7.4 Hz), 3.24 (2H, t, J=7.4 Hz), 738 (1H, d, J=3.2 Hz), 7.85 (1H, d, J=3.2 Hz), 8.20 (1H, s). MS (ES$^+$) 307 (M+1).

EXAMPLE 10

(4,4-Dimethyl-8-phenylthio-4,5-dihydrothieno[3,4-g]-1,2-benzisoxazol-6-yl) (pyrrolidin-1-yl) methanone Step 1: 6,6-Dimethyl-3-phenylthio-1-(pyrrolidin-1-ylcarbonyl)-4,5,6,7-tetrahydrobenzo[c]thiophen-4-one To a suspension of the 6,6-dimethyl-3-methanesulphonyl-1-(pyrrolidin-1-ylcarbonyl)-4,5,6,7-tetrahydrobenzo[c]thiophen-4-one (400 mg, 1.1 mmol) in EtOH (15 mL) was added thiophenol sodium salt (297 mg, 2.2 mmol). The mixture was stirred at room temperature for 3 h then the solvent evaporated. The residue was partitioned between EtOAc (20 mL) and water (30 mL). The organic phase was separated, dried (Na$_2$SO$_4$) and evaporated. The resultant oil was triturated with ether/hexane and the colourless solid (330 mg, 76%) collected by filtration. mp 140° C. $C_{21}H_{23}NO_2S_2$ requires: C, 65.42; H, 6.01; N, 3.63%. Found: C, 65.55; H, 5.77; N, 3.980%,. $^1$H NMR (360 MHz, CDCl$_3$) δ1.07 (6H, s), 1.86–1.90 (4H, m), 2.43 (2H, s), 2.78 (2H, s), 3.36–3.60 (4H, m), 7.43–7.51 (3H, m), 7.67–7.70 (2H, m). MS (ES$^+$) 386 (M+1).

Step 2: 6,6-Dimethyl-5-hydroxymethylene-3-phenylthio-1-(pyrrolidin-1-yl-carbonyl)-4,5,6,7-tetrahydrobenzo[c]thiophen-4-one In the same way as described in Example 1, Step 2, using 6,6-dimethyl-3-phenylthio-1-(pyrrolidin-1-ylcarbonyl)-4,5,6,7-tetrahydrobenzo[c]thiophen-4-one, the title compound 64 mg, 23%) was isolated as a cream solid. $^1$H NMR (250 MHz, CDCl$_3$) δ1.20 (6H, s), 1.85–1.91 (4H, m), 2.76 (2H, s), 3.30–3.60 (4H, m), 7.44–7.51 (3H, m), 7.61 (1H, d, J=10.4 Hz), 7.68–7.73 (2H, m),14.69 (1H, d, J=10.4 Hz). MS (ES$^+$) 414 (M+1).

Step 3: (4,4-Dimethyl-8-phenylthio-4,5-dihydrothieno[3,4-g]-1,2-benzisoxazol-6-yl)(pyrrolidin-1-yl)methanone In the same way as described in Example 1, Step 3, using 6,6-dimethyl-5-hydroxymethylene-3-phenylthio-1-(pyrrolidin-1-ylcarbonyl)-4,5,6,7-tetrahydrobenzo[c]thiophen-4-one, the isoxazole (33 mg, 52%) was isolated as a colourless solid. mp 49–52° C. $C_{22}H_{22}N_2O_2S_2$ requires: C, 64.36; H, 5.40; N, 6.82% Found: C, 64.22; H, 5.60; N, 6.46%. $^1$H NMR (360 MHz, (CDCl$_3$) δ1.28 (6H, s), 1.92–1.96 (4H, m), 2.91 (2H, s), 3.41–3.64 (4H, m), 7.25–7.34 (3H, m), 7.44–7.47 (2H, m), 8.19 (1H, s). MS (ES$^+$) 411 (M+1).

EXAMPLE 11

(4,4-Dimethyl-8-ethylthio-4,5-dihydrothieno[3,4-g]-1,2-benzisoxazol-6-yl)(pyrrolidin-1-yl)methanone Step 1: 6,6-Dimethyl-3-ethylthio-1-(pyrrolidin-1-ylcarbonyl)-4,5,6,7-tetrahydrobenzo[c]thiophen-4-one In the same way as described in Example 10, Step 1, using ethanethiol sodium salt, the title compound (381 mg, 59%) was isolated as a colourless solid. mp 129–132° C. $C_{17}H_{23}NO_2S_2$ requires: C, 60.50; H, 6.87; N, 4.15%. Found: C, 60.74; H, 6.76; N, 3.86%. $^1$H NMR (360 MHz, CDCl$_3$) δ1.04 (6H, s), 1.47 (3H, t, J=7.5 Hz), 1.94–1.98 (4H, m), 2.40 (2H, s), 2.83 (2H, s), 3.05 (2H, q, J=7.5 Hz), 3.58–3.62 (4H, mn). MS (ES$^+$) 338 (M+1).

Step 2: 6,6-Dimethyl-3-ethylthio-5-hydroxymethylene-1-(pyrrolidin-1-ylcarbonyl)-4,5,6,7-tetrahydrobenzo[c]thiophen-4-one In the same way as described in Example 1, Step 2, using 6,6-dimethyl-3-ethylthio-1-(pyrrolidin-1-ylcarbonyl)-4,5,6,7-tetrahydrobenzo[c]thiophen-4-one, the title compound (170 mg, 44%) was isolated as a pale yellow solid. $^1$H NMR (250 MHz, CDCl$_3$) δ1.18 (6H, s), 1.49 (3H, t, J=7.4 Hz), 1.93–1.99 (4H, mn), 2.80 (2H, s), 3.12 (2H, q, J=7.4 Hz), 3.53–3.70 (4H, mn), 7.57 (1H, d, J=10.4 Hz), 14.67 (1H, d, J=10.4 Hz). MS (ES$^+$) 352 (M+1)

Step 3: (4,4-Dimethyl-8-ethylthio-4,5-dihydrothieno[3,4-g]-1,2-benzisoxazol-6-yl)(pyrrolidin-1-yl)methanone In the same way as described in Example 1, Step 3, using 6,6-dimethyl-3-ethylthio-5-hydroxymethylene-1-(pyrrolidin-1-ylcarbonyl)-4,5,6,7-tetrahydrobenzo[c]thiophen-4-one, the isoxazole (80 mg, 47%) was isolated as a yellow solid. mp 91–93° C. $C_{18}H_{22}N_2O_2S_2$ requires: C, 59.64; H, 6.12; N, 7.73%. Found: C, 59.94; H, 5.86; N, 7.69%. $^1$H NMR (360 MHz, CDCl$_3$) δ1.19 (6H, s), 1.28 (3H, t, J=7.4 Hz), 1.87–1.92 (4H, m), 2.83 (2H, s), 2.98 (2H, q, J=7.4 Hz), 3.45–3.59 (4H, m), 8.13 (1H, s). MS (ES$^+$) 363 (M+1).

EXAMPLE 12

(4,4-Dimethyl-8-propylthio-4,5-dihydrothieno[3,4-g]-1,2-benzisoxazol-6-yl)(pyrrolidin-1-yl)methanone Step 1: 6,6-Dimethyl-3-propylthio-1-(pyrrolidin-1-ylcarbonyl)-4,5,6,7-tetrahydrobenzo[c]thiophen-4-one To a suspension of 6,6-dimethyl-3-methanesulphonyl-1-(pyrrolidin-1-ylcarbonyl)-4,5,6,7-tetrahydrobenzo[c]thiophen-4-one (500 mg, 1.4 mmol) in EtOH (15 mL) was added NaOH (0.71 mL of a 4 M solution, 2.8 mmol) followed by propanethiol (255 μL, 2.8 mmol). The mixture was stirred at room temperature for 2 h then evaporated. The residue was partitioned between EtOAc (20 mL) and water (20 mL). The organic layer was separated, dried (Na$_2$SO$_4$) and evaporated. The residue was triturated with ether and the colourless solid (380 mg, 77%) collected by filtration. mp 117–119° C. $C_{18}H_{25}NO_2S_2$ requires: C, 61.50; H, 7.17; N, 3.98%. Found: C, 61.48; H, 7.02; N, 3.97%. $^1$H NMR (250 MHz, CDCl$_3$) δ1.04 (6H, s), 1.10 (3H, t, J=7.3 Hz), 1.87 (2H, sextet, J=7.3 Hz), 1.93–1.99 (4H, m), 2.40 (2H, s), 2.83 (2H, s), 3.00 (2H, t, J=7.3 Hz), 3.57–3.63 (4H, m). MS (ES$^+$) 352 (M+1).

Step 2: 6,6-Dimethyl-5-hydroxymethylene-3-propylthio-1-(pyrrolidin-1-ylcarbonyl)-4,5,6,7-tetrahydrobenzo[c]thiophen-4-one In the same way as described in Example 1, Step 2, using 6,6-dimethyl-3-propylthio-1-(pyrrolidin-1-ylcarbonyl)-4,5,6,7-tetrahydrobenzo[c]thiophen-4-one, the title compound (140 mg, 43%) was isolated as a yellow solid. $^1$H NMR (250 MHz, CDCl$_3$) δ1.11 (3H, t, J=7.4 Hz), 1.18 (6H, s), 1.88 (2H, sextet, J=7.3 Hz), 1.93–1.99 (4H, m), 2.80 (2H, s), 3.05 (2H, t, J=7.3 Hz), 3.55–3.72 (4H, m), 7.57 (1H, d, J=10.4 Hz), 14.67 (1H, d, J=10.4 Hz). MS (ES$^+$) 380 (M+1).

Step 3: (4,4-Dimethyl-8-propylthio-4,5-dihydrothieno[3,4-g]-1,2-benzisoxazol-6-yl)(pyrrolidin-1-yl)methanone In the same way as described in Example 1, Step 3, using 6,6-dimethyl-5-hydroxymethylene-3-propylthio-1-(pyrrolidin-1-ylcarbonyl)-4,5,6,7-tetrahydrobenzo[c]thiophen-4-one, the isoxazole (14 mg, 10%) was isolated as a colourless solid. mp 72–76° C. $C_{19}H_{24}N_2O_2S_2$ requires: C, 60.61; H, 6.42; N, 7.44%. Found: C, 60.82; H, 6.15; N, 7.01%. $^1$H NMR (360 MHz, CDCl$_3$) δ1.04 (3H, t, J=7.4 Hz), 1.26 (6H, s), 1.72 (2H, sextet, J=7.4 Hz), 1.94–1.98 (4H, m), 2.89 (2H, s), 3.00 (2H, t, J=7.4 Hz), 3.51–3.65 (4H, m), 8.20 (1H, s). MS (ES$^+$) 377 (M+1).

EXAMPLE 13

4,4-Dimethyl-8-methylthio-6-(pyrid-2-yl)-4,5-dihydrothieno[3,4-g]-1,2-benzisoxazole, Step 1: 6,6-Dimethyl-3-methylthio-1-(pyrid-2-yl)-4,5,6,7-tetrahydrobenzo[c]thiophen-4-one 1-Bromo-6,6-dimethyl-3-methylthio-4,5,6,7-tetrahydrobenzo[c]thiophen-4-one (300 mg, 1 mmol) was dissolved in dioxane (25 mL), and 2-(tri-n-butylstannyl)pyridine (550 mg, 1.35 mmol) was added. The solution was de gassed with nitrogen then tetrakis (tri-phenylphosphine) palladium (30 mg, 0.025 mmol) was added and the solution refluxed for 16 h. The solvent was then removed in vacuo and the residue triturated with a mixture of ethyl acetate and hexane (1:3). After filtration the solid product was washed with a little diethyl ether to give the title compound as a white solid (170 mg, 57%). mp 217–220° C. Found: C, 63.02; H, 5.64; , 4.47%. $C_{16}H_{17}NOS_2$ requires: C, 63.36; H, 5.61; N, 4.62%. $^1$H NMR (250 MHz, CDCl$_3$)δ1.08 (6H, s), 2.44 (2H, s), 2.65 (3H, s), 2.93 (2H, s), 7.18 (1H, m), 7.47 (1H, d, J=8Hz), 7.71–7.77 (1H, m), 8.61–8.63 (1H, m). MS (ES$^+$) 304 (M+1).

Step 2: 6,6-Dimethyl-5-hydroxymethylene-3-methylthio-1-(pyrid-2-yl)-4,5,6,7-tetrahydrobenzo[c]thiophen-4-one To a solution of sodium hydride (108 mg of a 60% dispersion in mineral oil, 2.7 mmol) and ethyl formate (0.55 mL, 6.8 mmol) at 0C in THF (5 mL) was added a solution of 6,6-dimethyl-3-methylthio-1-(pyrid-2-yl)-4,5,6,7-tetrahydrobenzo[c]thiophen-4-one (205 mg, 0.68 mmol) in THF (5 mL). The mixture was stirred at room temperature for 2 h then more sodium hydride (50 mg of a 60% dispersion in mineral oil, 1.3 mmol) and ethyl formate (0.55 mL, 6.8 mmol) were added. The mixture was stirred for a further 2 h before MeOH (0.2 mL) was added and the mixture evaporated in vacuo. The residue was dissolved in water (20 mL) and the undissolved solid filtered off. The mixture was acidified to pH 1 using 1M HCl then neutralised with Na$_2$CO$_3$. The mixture was partitioned between EtOAc (20 mL) and water (10 mL) and the organic layer separated and dried (MgSO$_4$). The solvent was evaporated and the residue triturated with ether to afford the title compound (90 mg, 40%) as a yellow solid. $^1$H NMR (250 MHz, CDCl$_3$) δ1.21 (6H, s), 2.70 (3H, s), 2.93 (2H, s), 7.16–7.22 (1H, m), 7.4.3 (1H, d, J=8.0 Hz), 7.57 (1H, d, J=10.4 Hz), 7.74 (1H, d of t, J=7.7 and 1.8 Hz), 8.62–8.65 (1H, m), 14.68 (1H, d, J=10.4 Hz). MS (ES$^+$) 332 (M+1).

Step 3: 4,4-Dimethyl-8-methylthio-6-(pyrid-2-yl)-4,5-dihydrothieno[3,4-g]-1,2-benzisoxazole In the same way as described in Example 1, Step 3, using 6,6-dimethyl-5-hydroxymethylene-3-methylthio-1-(pyrid-2-yl)-4,5,6,7 -tetrahydrobenzo[c]thiophen-4-one, the isoxazole (60 mg, 70%) was isolated as a yellow solid. mp 153–155° C. $C_{17}H_{16}N_2OS_2.0.1(H_2O)$ requires: C, 61.83; H, 4.94; N, 8.48%. Found: C, 61.69; H, 4.84; N 8.13%. $^1$H NMR (360 MHz, CDCl$_3$) δ1.28 (6H, s), 2.68 (3H, s), 3.05 (2H, s), 7.19–7.23 (1H, m), 7.46 (1H, d, J=8.0 Hz), 7.75 (1H, d of t, J=7.7 and 1.8 Hz), 8.20 (1H, s), 8.62–8.66 (1H, m). MS (ES$^+$) 329 (M+1).

EXAMPLE 14

4,4-Dimethyl-8-methylthio-6-(pyrid-3-yl)-4,5-dihydrothieno[3,4-g]-1,2-benzisoxazole Step 1: 6,6-Dimethyl-3-methylthio-1-(pyrid-3-yl)-4,5,6,7-tetrahydrobenzo[c]thiophen-4-one In the same way as described in Example 13, Step 1, using 3-(tri-n-butylstannyl)pyridine, the title compound (224 mg, 29%) was isolated as a colourless oil. $^1$H NMR (250 MHz, CDCl$_3$) δ1.04 (6H, s), 2.44 (2H, s), 2.63 (3H, s), 2.76 (2H, s), 7.38 (1H, dd, J=7.9 and 4.8 Hz), 7.72 (1H, t of d, J=7.9 and 1.9 Hz), 8.52–8.60 (1H, m), 8.70 (1H, d, J=1.9 Hz). MS (ES$^+$) 304 (M+1).

Step 2: 6,6-Dimethyl-5-hydroxymethylene-3-methylthio-1-(pyrid-3-yl)-4,5,6,7-tetrahydrobenzo[c]thiophen-4-one In the same way as described in Example 13, Step 2, using 6,6-dimethyl-3-methylthio-1-(pyrid-3-yl)-4,5,6,7-tetrahydrobenzo[c]thiophen-4-one, the title compound (80 mg, 34%) was isolated as an orange solid. mp 154–156° C. $^1$H NMR (250 MHz, CDCl$_3$) δ1.17 (6H, s), 2.68 (3H, s), 2.73 (2H, s), 7.38 (1H, dd, J=7.9 and 4.8 Hz), 7.60 (1H, d, J=10.4 Hz), 7.71 (1H, t of d, J=7.9 and 1.9 Hz), 8.54–8.61 (1H, m), 8.70 (1H, d, J=1.9 Hz), 14.74 (1H, d, J=10.4 Hz). MS (ES$^+$) 332 (M+1).

Step 3: 4,4-Dimethyl-8-methylthio-6-(pyrid-3-yl)-4,5-dihydrothieno[3,4-g]-1,2-benzisoxazole In the same way as described in Example 13, Step 3, using 6,6-dimethyl-5-hydroxymethylene-3-methylthio-1-(pyrid-3-yl)-4,5,6,7-tetrahydrobenzo[c]thiophen-4-one, the isoxazole (42 mg, 53%) was isolated as a yellow solid. mp 123–125° C. $C_{17}H_{16}N_2OS_2.0.4(H_2O)$ requires: C, 60.83; H, 5.05; N, 8.36% Found: C, 60.55; H, 4.73; N, 8.03%. $^1$H NMR (360 MHz, CDCl$_3$) δ1.22 (6H, s), 2.67 (3H, s), 2.80 (2H, s), 7.38 (1H, dd, J=7.7 and 4.9 Hz), 7.71 (1H, d of t, J=7.9 and 1.9 Hz), 8.21 (1H, s), 8.59–8.64 (1H, m), 8.70 (1H, d, J=1.9 Hz). MS (ES$^+$) 329 (M+1).

EXAMPLE 15

4,4-Dimethyl-6-(1-methylpyrazol-3-yl)-8-methylthio-4,5-dihydrothieno[3,4-g]-1,2-benzisoxazole Step 1: 6,6-Dimethyl-5-hydroxymethylene-1-(1-methylpyrazol-3-yl)-3-methylthio-4,5,6,7-tetrahydrobenzo[c]thiophen-4-one In the same way as described in Example 1, Step 2, using 6,6-dimethyl-1-(1-methylpyrazol-3-yl)-3-methylthio-4,5,6,7-tetrahydrobenzo[c]thiophen-4-one, the title compound (767 mg, 88%) was isolated as a yellow solid. mp 145–148° C. $C_{16}H_{18}O_2N_2S_2$ requires: C, 57.46; H, 5.42; N, 8.38%. Found: C, 57.69; H, 5.50; N, 8.13%. $^1$H NMR (360 MHz, CDCl$_3$) δ1.16 (6H, s), 2.49 (2H, s), 2.65 (3H, s), 3.81 (3H, s), 6.30 (1H, d, J=1.9 Hz), 7.54 (1H, d, J=1.9 Hz), 7.60 (1H, d, J=10.4 Hz), 14.71 (1H, d, J=10.4 Hz). MS (ES$^+$) 335 (M+1).

Step 2: 4,4-Dimethyl-6-(1-methylpyrazole-3-yl)-8-methylthio-4,5-dihydrothieno[3,4-g]-1,2-benzisoxazole In the same way as described in Example 1, Step 3, using 6,6-dimethyl-5-hydroxymethylene-1-(1-methylpyrazol-3-yl)-3-methylthio-4,5,6,7-tetrahydrobenzo[c]thiophen-4-one, the isoxazole (200 mg, 100%) was isolated as a cream solid. mp 128–130° C. $^1$H NMR (360 MHz, CDCl$_3$) δ1.24 (6H, s), 2.58 (2H, s), 2.66 (3H, s), 3.84 (3H, s), 6.31 (1H, d, J=1.9 Hz), 7.55 (1H, d, J=1.9 Hz), 8.20 (1H, s). MS (ES$^+$) 332 (M+1).

EXAMPLE 16

4,4-Dimethyl-8-methylthio-6-(1-methyl-1,2,4-triazol-3-yl)-4,5-dihydrothieno[3,4-g]-1,2-benzisoxazole Step 1: 6,6-Dimethyl-3-methylthio-4,5,6,7-tetrahydrobenzo[c]thiophen-4-one-1-carboximidic acid ethyl ester hydrochloride A solution of 1-cyano-6,6-dimethyl-3-methylthio-4,5,6,7-tetrahydrobenzo[c]thiophen-4-one (300 mg, 1.19 mmol) in saturated ethanolic hydrogen chloride solution (50 mL) was stirred at 20° C. for 18 h. The solvent was removed in vacuo and the residue was triturated with ethyl acetate. The product was filtered off, washed with ether and dried to yield the title compound as a white solid (350 mg, 98%). mp 134–136° C. $^1$H NMR (250 MHz, d$_6$-DMSO) δ1.00 (6H, s), 1.44 (3H, t, J=7.0Hz), 2.45 (2H, s), 2.67 (3H, s), 3.00 (2H, s), 4.52 (2H, q, J=7.0Hz). MS (ES$^+$) 298 (M+1).

Step 2: 6,6-Dimethyl-3-methylthio-1-(1-methyl-1,2,4-triazol-3-yl)-4,5,6,7-tetrahydrobenzo[c]thiophen-4-one 6,6-Dimethyl-3-methylthio-4,5,6,7-tetrahydrobenzo[c]thiophen-4-one-1-carboximidic acid ethyl ester (1.0 g, 3.37 mmol) was dissolved in ethanol (60 mL) and methyl hydrazine (0.16 g, 3.37 mmol) was added. The solution was heated at 50° C. for 7 h then evaporated to dryness and the residue was taken up in formic acid (20 mL). The solution was heated at 100° C. for 16 h then evaporated to dryness. The residue was dissolved in DCM and washed with saturated K$_2$CO$_3$ solution, then evaporated to dryness. The crude product was chromatographed on silica gel, eluting with ethyl acetate to yield the title compound as a yellow solid (0.15 g, 15%). mp 146–148° C. $C_{14}H_{17}N_3OS_2$ requires: C, 54.70; H, 5.77; N, 13.27%. Found: C, 54.55; H, 5.46; N, 13.27%. $^1$H NMR (250 MHz, CDCl$_3$) δ1.05 (6H, s), 2.44 (2H, s), 2.63 (3H, s), 2.74 (2H, s), 3.96 (3H, s), 7.98 (1H, s). MS (ES$^+$) 308 (M+1).

Step 3: 6,6-Dimethyl-5-hydroxymethylene-3-methylthio-1-(1-methyl-1,2,4-triazol-3-yl)-4,5,6,7-tetrahydrobenzo[c]thiophen-4-one In the same way as described in Example 1, Step 2, using 6,6-dimethyl-3-methylthio-1-(1-methyl-1,2,4-triazol-3-yl)-4,5,6,7-tetrahydrobenzo[c]thiophen-4-one, the title compound (50 mg, 38%) was isolated as a colourless solid. $^1$H NMR (360 MHz, CDCl$_3$) δ1.19 (6H, s), 2.67 (3H, s), 2.73 (2H, s), 3.94 (3H, s), 7.61 (1H, d, J=10.4 Hz), 7.97 (1H, s), 14.64 (1H, d, J=10.4 Hz). MS (ES$^+$) 336 (M+1).

Step 4: 4,4-Dimethyl-8-methylthio-6-(1-methyl-1,2,4-triazol-3-yl)-4,5-dihydrothieno[3,4-g]-1,2-benzisoxazole In the same way as described in Example 1, Step 3, using 6,6-dimethyl-5-hydroxymethylene -3-methylthio-1-(1-methyl-1,2,4-triazol-3-yl) -4,5,6,7-tetrahydrobenzo[c]thiophen-4-one, the isoxazole (8 mg, 16%) was isolated as a colourless solid. $^1$H NMR (360 MHz, CDCl$_3$) δ1.27 (6H, s), 2.68 (3H, s), 2.87 (2H, s), 3.99 (3H, s), 7.98 (1H, s), 8.22 (1H, s). MS (ES$^+$) 333 (M+1).

We claim:

1. A compound of formula (I) or a pharmaceutically acceptable salt thereof:

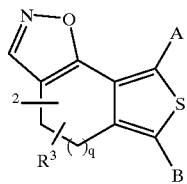

where A is $C_{1-6}$alkyl, $C_{2-6}$alkenyl, $C_{2-6}$alkynyl, $C_{3-6}$cycloalkyl, aryl$C_{1-6}$alkyl, aryl, $S(O)_pR^1$, $OR^1$ or $NR^1R^{12}$;

B is a 5-membered ring having one or two unsaturations containing 1, 2, 3 or 4 heteroatoms chosen from O, N and S provided that not more than one heteroatom is other than N, or a 6-membered aromatic ring containing 1 or 2 nitrogen atoms, which ring is optionally substituted by one or more substituents independently chosen from: $C_{1-6}$alkyl; $C_{1-6}$haloalkyl; halogen; $S(O)_pR^4$; $COR^5$; and aryl or aryl $C_{1-6}$alkyl wherein the aryl ring is optionally substituted by one, two or three substituents independently chosen from halogen, $CF_3$, $OCH_3$, nitro and cyano; or B is a group $C(O)NR^{10}R^{11}$;

$R^1$ is hydrogen; $C_{1-6}$alkyl, $C_{2-6}$alkenyl, $C_{2-6}$alkynyl, $C_{3-6}$cycloalkyl or $C_{3-6}$cycloalkenyl each of which is optionally substituted by amino, $C_{1-6}$alkylamino, di($C_{1-6}$alkyl)amino, $C_{1-6}$alkoxy, $C_{1-6}$alkylaminocarbonyl, one, two or three hydroxy groups, one, two or three halogen atoms or a four, five or six-membered saturated heterocyclic ring containing a nitrogen atom and optionally either an oxygen atom or a further nitrogen atom which ring is optionally substituted by $C_{1-4}$alkyl on the further nitrogen atom; aryl, aryl$C_{1-6}$alkyl, aryl$C_{2-6}$alkenyl or aryl$C_{2-6}$alkynyl optionally substituted on the aryl ring by halogen nitro, cyano, $C_{1-6}$alkylcarbonylamino, hydroxy or $C_{1-6}$alkoxy; or a five-membered aromatic ring containing 1, 2, 3 or 4 heteroatoms chosen from O, N and S provided that not more than one heteroatom is other than N, or a six-membered aromatic ring containing 1, 2, 3 or 4 nitrogen atoms, either of which rings is optionally substituted by halogen, $C_{1-6}$alkoxy, $C_{1-6}$alkylthio, aryl, $C_{1-6}$alkyl, $C_{2-6}$alkenyl or $C_{2-6}$alkynyl;

$R^2$ and $R^3$ are independently hydrogen or $C_{1-6}$alkyl or together with the carbon atom to which they are attached form a $C_{3-8}$cycloalkyl group;

$R^4$ is hydrogen, $C_{1-8}$alkyl, $C_{2-8}$alkenyl, $C_{2-8}$alkynyl, aryl or $CH_2(CO)_mNR^8R^9$;

$R^5$ is $NR^6R^7$, ($C_{1-6}$alkyl or $C_{1-6}$alkoxy;

$R^6$ is independently as defined for $R^4$;

$R^7$ is aryl optionally substituted by halogen, nitro or cyano;

$R^8$ is hydrogen, $C_{1-6}$alkyl, $C_{3-6}$cycloalkyl, $C_{3-6}$cycloalkenyl, $C_{2-6}$alkenyl, $C_{2-6}$alkynyl;

aryl$C_{1-6}$alkyl, aryl$C_{2-6}$alkenyl or aryl$C_{2-6}$alkynyl optionally substituted on the aryl ring by halogen, nitro or cyano; thiophene or pyridine;

$R^9$ is $C_{1-6}$alkyl; $C_{2-6}$alkenyl; $C_{2-6}$alkynyl; or phenyl optionally substituted by one, two or three substituents independently chosen from halogen, $CF_3$, $OCH_3$, nitro and cyano;

$R^{10}$ and $R^{11}$ are individually hydrogen, $C_{1-6}$alkyl, $C_{2-6}$alkenyl, $C_{2-6}$alkynyl or $C_{3-8}$cycloalkyl or $R^{10}$ and $R^{11}$, together with the nitrogen atom to which they are attached, form a saturated 4 to 8 membered ring optionally containing an oxygen atom or a further nitrogen atom as a ring member, the further nitrogen atom being unsubstituted or substituted by $C_{1-4}$alkyl, $C_{2-4}$alkenyl or $C_{2-4}$alkynyl;

$R^{12}$ is hydrogen or $C_{1-6}$alkyl;

m is zero or 1;

p is zero, 1 or 2;

q is 0, or 2; and r is 0, 1 or 2.

2. A compound according to claim 1 wherein B is a 5- or 6-membered optionally substituted aromatic ring.

3. A compound according to claim 1 wherein A is $S(O)_pR^1$.

4. A compound according to claim 1 in which:

A is $S(O)_pR^1$ or $OR^1$;

B is a thiazole, pyrazole, pyrimidine, tetrazole, triazole, oxadiazole, oxazole, pyridine, imidazole or pyrazine which is unsubstituted or substituted by $C_{1-6}$alkyl or halogen, or B is $C(O)NR^{10}R^{11}$;

$R^1$ is $C_{1-6}$alkyl or phenyl;

$R^2$ and $R^3$ are independently hydrogen or methyl;

$R^{10}$ and $R^{11}$ are independently hydrogen, $C_{1-4}$alkyl or $C_{1-6}$cycloalkyl or $R^{10}$ and $R^{11}$, together with the nitrogen atom to which they are attached, form a saturated 5- to 7-membered ring optionally containing an oxygen atom or a further nitrogen atom at the 4-position, the further nitrogen atom being unsubstituted or substituted with $C_{1-4}$alkyl;

p is zero or 2; and q is one.

5. A pharmaceutical composition comprising a compound according to claim 1 or a pharmaceutically acceptable salt thereof and a pharmaceutically acceptable excipient.

6. A method of treatment or prevention of a condition which requires the administration of a cognition enhancing agent which comprises administering to a subject suffering from or prone to such a condition a therapeutically or prophylactically effective amount of a compound according to claim 1 or a pharmaceutically acceptable salt thereof.

* * * * *